United States Patent
Xiao

(10) Patent No.: US 7,049,089 B2
(45) Date of Patent: May 23, 2006

(54) REGULATION OF HUMAN PLC DELTA-1

(75) Inventor: Yonghong Xiao, Cambridge, MA (US)

(73) Assignee: Bayer Aktiengesellschaft, Leverkusen (DE)

(*) Notice: Subject to any disclaimer, the term of this patent is extended or adjusted under 35 U.S.C. 154(b) by 510 days.

(21) Appl. No.: 10/276,339

(22) PCT Filed: May 29, 2001

(86) PCT No.: PCT/EP01/06087

§ 371 (c)(1),
(2), (4) Date: Nov. 27, 2002

(87) PCT Pub. No.: WO01/92488

PCT Pub. Date: Dec. 6, 2001

(65) Prior Publication Data

US 2003/0191060 A1    Oct. 9, 2003

Related U.S. Application Data

(60) Provisional application No. 60/278,742, filed on Mar. 27, 2001, provisional application No. 60/207,277, filed on May 30, 2000.

(51) Int. Cl.
*C12Q 1/48* (2006.01)
*C12N 9/00* (2006.01)

(52) U.S. Cl. ............................ 435/15; 435/193; 514/12

(58) Field of Classification Search ............... 435/15, 435/193; 536/23.2
See application file for complete search history.

(56) References Cited

FOREIGN PATENT DOCUMENTS

| WO | WO 01/53468 | 7/2001 |
|----|-------------|--------|
| WO | WO 01/55300 | 8/2001 |
| WO | WO 01/66764 | 9/2001 |

OTHER PUBLICATIONS

Database EM_(Online) EMBL: Accession No: AI369426, Jan. 13, 1999. "Homo sapiens cDNA clone IMAGE:2019525 3 similar Phospholipase C-Delta 1.", XP002197071.

Cheng Hwei-Fang et al., "Cloning and identification of amino acid residues of human phospholipase C-delta-1 essential for catalysis", Journal of Biological Chemistry, Mar. 10, 1995, vol. 270, No. 10, pp. 5495-5505, XP002197068.

Wang Tieli et al. "The pleckstrin homology domain of phospholipase C-beta2 links the binding of Gbetagamma to activation of the catalytic core", Journal of Biological Chemistry, Mar. 17, 2000, vol. 275, No. 11, pp 7466-7469, XP002197069.

Ghosh Smita et al., "Phospholipase C isoforms delta-1 and delta-3 from human fibroblasts", Protein Expression and Purification, Mar. 1997, vol. 9, No. 2, pp. 262-278, XP001073550.

Database EMBL (Online), Accession No: AAU18956, Nov. 21, 2001, Human Genome Science, "Novel Lung Cancer Antigen", XP002197416.

*Primary Examiner*—Rebecca E. Prouty
*Assistant Examiner*—Mohammad Meah
(74) *Attorney, Agent, or Firm*—Banner & Witcoff, Ltd.

(57) ABSTRACT

Reagents which regulate human PLC delta-1 activity and reagents which bind to human PLC delta-1 gene products can be used, inter alia, to treat COPD, congestive heart failure, hypertension, and cancer, and a variety of conditions in which signal transduction is impaired.

3 Claims, 15 Drawing Sheets

Fig. 1 cggccgctggaggcgttgccgccgcccgcccgaggagccccggtggccgcccaggtcgc
agcccaagtcgcggcgccggtcgctctcccgtccccgccgactccctccgatggcggcac
caagaggcccgggctgcgggcgctgaagaagatgggcctgacggaggacgaggacgtgcg
cgccatgctgcggggctcccggctccgcaagatccgctcgcgcacgtggcacaaggagcg
gctgtaccggctgcaggaggacggcctgagcgtgtggttccagcggcgcatcccgcgtgc
gccatcgcagcacatcttcttcgtgcagcacatcgaggcggtccgcgagggccaccagtc
cgagggcctgcggcgcttcggggggtgccttcgcgccagcgcgctgcctcaccatcgcctt

Fig. 2

GRWRRCRRPPEEPPVAAQVAAQVAAPVALPSPPTPSDGGTKRPGLRALKK
MGLTEDEDVRAMLRGSRLRKIRSRTWHKERLYRLQEDGLSVWFQRRIPRA
PSQHIFFVQHIEAVREGHQSEGLRRFGGAFAPARCLTIA

Fig. 3 gcggccgctg gaggcgttgc cgccgcccgc ccgaggagcc cccggtggcc gcccaggtcg cagcccaagt
cgcggcgccg gtcgctctcc cgtccccgcc gactccctcc gatggcggca ccaagaggcc cgggctgcgg
gcgctgaaga agatgggcct gacggaggac gaggacgtgc gcgccatgct gcggggctcc cggctccgca
agatccgctc gcgcacgtgg cacaaggagc ggctgtaccg gctgcaggag gacggcctga gcgtgtggtt
ccagcggcgc atcccgcgtg cgccatcgca gcacatcttc ttcgtgcagc acatcgaggc ggtccgcgag
ggccaccagt ccgagggcct gcggcgcttc ggggtgcct tcgcgccagc gcgctgcctc accatcgcct
tcaagggccg ccgcaagaac ctggacctgg cggcgccac ggctgaggaa gcgcagcgct gggtgcgcgg
tctgaccaag ctcc

Fig. 4

GRWRRCRRPP EEPPVAAQVA AQVAAPVALP SPPTPSDGGT KRPGLRALKK MGLTEDEDVR AMLRGSRLRK
IRSRTWHKER LYRLQEDGLS VWFQRRIPRA PSQHIFFVQH IEAVREGHQS EGLRRFGGAF APARCLTIAF
KGRRKNLDLA APTAEEAQRW VRGLTKL

Fig. 5 gcggccgctg gaggcgttgc cgccgcccgc ccgaggagcc cccggtggcc gcccaggtcg cagcccaagt
cgcggcgccg gtcgctctcc cgtccccgcc gactccctcc gatggcggca ccaagaggcc cgggctgcgg
gcgctgaaga agatgggcct gacggaggac gaggacgtgc gcgccatgct gcggggctcc cggctccgca
agatccgctc gcgcacgtgg cacaaggagc ggctgtaccg gctgcaggag gacggcctga gcgtgtggtt
cagcggcgca tcccgcgtgc gccatcgcag cacatcttct tcgtgcagca catcgaggcg gtccgcgagg
gccaccagtc cgagggcctg cggcgcttcg ggggtgcctt cgcgccagcg cgctgcctca ccatcgcctt
caagggccgc cgcaagaacc tggacctggc ggcgcccacg gctgaggaag cgcagcgctg ggtgcgcggt

Fig. 6 gcggccgctg gaggcgttgc cgccgcccgc ccgaggagcc cccggtggcc gcccaggtcg cagcccaagt
cgcggcgccg gtcgctctcc cgtccccgcc gactccctcc gatggcggca ccaagaggcc cgggctgcgg
gcgctgaaga agatgggcct gacggaggac gaggacgtgc gcgccatgct gcggggctcc cggctccgca
agatccgctc gcgcacgtgg cacaaggagc ggctgtaccg gctgcaggag gacggcctga gcgtgtggtt
ccagcggcgc atcccgcgtg cgccatcgca gcacatcttc ttcgtgcagc acatcgaggc ggtccgcgag
ggccaccagt ccgagggcct gcggcgcttc ggggtgcct tcgcgccagc gcgctgcctc accatcgcct
tcaagggccg ccgcaagaac ctggacctgg cggcgccac ggctgagga

Fig. 7

```
gcggccgctg gaggcgttgc cgccgcccgc ccgaggagcc cccagtggcc gcccaggtcg cagcccaagt
cgcggcgccg gtcgctctcc cgtccccgcc gactccctcc gatggcggca ccaagaggcc cgggctgcgg
gcgctgaaga agatgggcct gacggaggac gaggacgtgc gcgccatgct gcggggctcc cggctccgca
agatccgctc gcgcacgtgg cacaaggagc ggctgtaccg gctgcaggag gacggcctga gcgtgtggtt
ccagcggcgc atgccgcgtg cgccatcgca gcacatcttc ttcgtgcagc acatcgaggc ggtccgcgag
ggccaccagt ccgagggcct gcggcgctt
```

Fig. 8

```
gcggccgctg gaggcgttgc gccgcccgcc cgaggagccc ccagtggccg cccaggtcgc agcccaagtc
gcggcgccgg tcgctctccc gtccccgccg actccctccg atggcggcac caagaggccc gggctgcggg
gcgtgaagaa gatgggcctg acggaggacg aggacgtgcg cgccatgctg cggggctccc ggctccgcaa
gatccgctcg cgcacgtggg acaaggagcg gctgtaccgg ctgcaggagg acggcctgag cgtgtggttc
cagcggcgca tc
```

Fig. 9

WIHSYLHRADSNQDSKMSFKEIKSLLRMVNVDMNDMYAYLLFK

Fig. 10

```
atgggcctga cggaggacga ggacgtgcgc gccatgctgc ggggctcccg gctccgcaag atccgctcgc
gcacgtggca caaggagcgg ctgtaccggc tgcaggagga cggcctgagc gtgtggttcc agcggcgcat
cccgcgtgcg ccatcgcagc acatcttctt cgtgcagcac atcgaggcgg tccgcgaggg ccaccagtcc
gagggcctgc ggcgcttcgg gggtgccttc gcgccagcgc gctgcctcac catcgccttc aagggccgcc
gcaagaacct ggacctggcg gcgcccacgg ctgaggaagc gcagcgctgg gtgcgcggtg ggggtgactt
accagccagt tacctgaggg ctggggcag cctggcgtgt tgctgttatt tcctgagcac ccacacctgg
atccactcct atctgcaccg ggctgactcc aaccaggaca gcaagatgag cttcaaggag atcaagagcc
tgctgagaat ggtcaacgtg gacatgaacg acatgtacgc ctacctcctc ttcaaggagt gtgaccactc
caacaacgac cgtctagagg gggctgagat cgaggagttc ctgcggcggc tgctgaagcg gccggagctg
gaggagatct tccatcagta ctcgggcgag gaccgcgtgc tgagtgcccc tgagctgctg gagttcctgg
aggaccaggg cgaggagggc gccacactgg cccgcgccca gcagctcatt cagacctatg agctcaacga
gacagccaag cagcatgagc tgatgacact ggatggcttc atgatgtacc tgttgtcgcc ggaggggct
gccttggaca acacccacac gtgtgtgttc caggacatga accagcccct tgcccactac ttcatctctt
cctcccacaa cacctatctg actgactccc agatcggggg gcccagcagc accgaggcct atgttagggc
ctttgcccag ggatgccgct gcgtggagct ggactgctgg gaggggccag gaggggagcc cgtcatctat
catgccata ccctcacctc caagattctc ttccgggacg tggtccaagc cgtgcgcgac catgccttca
cgctgtcccc ttaccctgtc atcctatccc tggagaacca ctgcgggctg gagcagcagg ctgccatggc
ccgccacctc tgcaccatcc tggggacat gctggtgaca caggcgctgg actccccaaa tcccgaggag
ctgccatccc cagagcagct gaagggccgg gtcctggtga agggaaagaa gttgcccgct gctcggagcg
aggatggccg ggctctgtcg gatcgggagg aggaggagga ggatgacgag gaggaagaag aggaggtgga
ggctgcagcg cagaggcggc tggtgagagc tgggatggat ctccccggag ctgtcggccc tggctgtgta
ctgccacgcc acccgcctgc gaccctgcac cctgccccca acgccccaca accctgccag gtcagctccc
tcagcgagcg caaagccaag aaactcattc gggaggcagg gaacagcttt gtcaggcaca atgcccgcca
gctgacccgc gtgtacccgc tggggctgcg gatgaactca gccaactaca gtccccagga gatgtggaac
tcgggctgtc agctggtggc cttgaacttc cagacgccag gctacgagat ggacctcaat gccgggcgct
tcctagtcaa tgggcagtgt ggctacgtcc taaaacctgc ctgcctgcgg caacctgact cgacctttga
ccccgagtac ccaggacctc ccagaaccac tctcagcatc caggtgctga ctgcacagca gctgcccaag
ctgaatgccg agaagccaca ctccattgtg gaccccctgg tgcgcattga gatccatggg gtgccgcag
actgtgcccg gcaggagact gactacgtgc tcaacaatgg cttcaacccc gctggggggc agacctgca
gttccagctg cgggctccgg agctggcact ggtccggttt gtggtggaag attatgacgc cacctcccc
```

Fig. 10 (cont'd)

```
aatgactttg tgggccagtt tacactgcct cttagcagcc taaagcaagg gtaccgccac atacacctgc
tttccaagga cggggcctca ctgtcaccag ccacgctctt catccaaatc cgcatccagc gctcctga
```

Fig. 11

```
MDSGRDFLTL HGLQDDPDLQ ALLKGSQLLK VKSSSWRRER FYKLQEDCKT IWQESRKVMR SPESQLFSIE
DIQEVRMGHR TEGLEKFARD IPEDRCFSIV FKDQRNTLDL IAPSPADAQH WVQGLRKIIH HSGSMDQRQK
LQHWIHSCLR KADKNKDNKM NFKELKDFLK ELNIQVDDGY ARKIFRECDH SQTDSLEDEE IETFYKMLTQ
RAEIDRAFEE AAGSAETLSV ERLVTFLQHQ QREEEAGPAL ALSLIERYEP SETAKAQRQM TKDGFLMYLL
SADGNAFSLA HRRVYQDMDQ PLSHYLVSSS HNTYLLEDQL TGPSSTEAYI RALCKGCRCL ELDCWDGPNQ
EPIIYHGYTF TSKILFCDVL RAIRDYAFKA SPYPVILSLE NHCSLEQQRV MARHLRAILG PILLDQPLDG
VTTSLPSPEQ LKGKILLKGK KLGGLLPAGG ENGSEATDVS DEVEAAEMED EAVRSQVQHK PKEDKLKLVP
ELSDMIIYCK SVHFGGFSSP GTSGQAFYEM ASFSESRALR LLQESGNGFV RHNVSCLSRI YPAGWRTDSS
NYSPVEMWNG GCQIVALNFQ TPGPEMDVYL GCFQDNGGCG YVLKPAFLRD PNTTFNSRAL TQGPWWRPER
LRVRIISGQQ LPKVNKNKNS IVDPKVIVEI HGVGRDTGSR QTAVITNNGF NPRWDMEFEF EVTVPDLALV
RFMVEDYDSS SKNDFIGQST IPWNSLKQGY RHVHLLSKNG DQHPSATLFV KISIQD
```

Fig. 12

```
vikeGwLlkkskswkkRyfvLfnnvLlyykdskkkpkgsipLsgcqvekpdkncFeirtdrtlllqaeseeerkeWvk
aiqsa
```

Fig. 13

```
BLASTP - Query= AI799721_TR3; Hit = swissnew|P10688|PIP6_RAT

This hit is scoring at : 2e-25 (expectation value)

Alignment length (overlap) : 117

Identities : 43 %

Scoring matrix : BLOSUM62 (used to infer consensus pattern)

Database searched : nrdb

Q:  52 GLTEDEDVRAMLRGSRLRKIRSRTWHKERLYRLQEDGLSVWFQ-RRIPRAPSQHIFFVQH
       GL.:D.D::A:L:GS:L K::S..W..ER.Y:LQED   ::W  : R:: R:P....:F :::
H:  12 GLQDDPDLQALLKGSQLLKVKSSWRRERFYKLQEDCKTIWQESRKVMRSPESQLFSIED

IEAVREGHQSEGLRRFGGAFAPARCLTIAFKGRRKNLDLAAPTAEEAQRWVRGLTKL    167
       I:.VR GH::EGL..:F.    RC.:I.FK:.R:.LDL.AP:...:AQ.WV:GL.K:
       IQEVRMGHRTEGLEKFARDIPEDRCFSIVFKDQRNTLDLIAPSPADAQHWVQGLRKI    128

PH (Pleckstrin Homology) domain
```

Fig. 14

```
HMMPFAM - alignment of AI799721_TR3 against pfam|hmm|PH

This hit is scoring at : 15.1; e=0.0081

Scoring matrix : BLOSUM62 (used to infer consensus pattern)

Q:  61 AMLRGSRLRKIrsrTWHKERLYRLQEDGLSVWFQRRiprAPSQHIFFVQHIeAVREgHQs
       .:  .G   L:K         K:R.:   L  .:         .:    .:  .V.:  .

H:   1 vikeGwLlkks...kswkkRyfvLfnnvLlyykdsk...kkpkgsipLsgc.qvek.pd.

eglrrfggafapARCLTIAPkGRrkNLDLAAPTABEAQRWVRGLTKL   167
       ..C..I.   .R    .L L.A.:.EE.:.WV:.:...

............kmcFeirt.dr..tlllqaeseeerkeWvkaiqsa    83
```

Fig. 15

Genomic sequence search:

```
tBLASTn:  Query = PIP6_RAT|P10688;  Hit = AC024047 (human htgs)
    (The only possible additional coding exon in genomic DNA hit)
Query: 144    WIHSCLRKADKNKDNKMNFKELKDFLKELNIQVDDGYARKIFR  186
              WIHS L +AD N+D+KM+FKE+K   L+ +N+ ++D YA   +F+
Sbjct: 82207  WIHSYLHRADSNQDSKMSFKEIKSLLRMVNVDMNDMYAYLLFK  82335
```

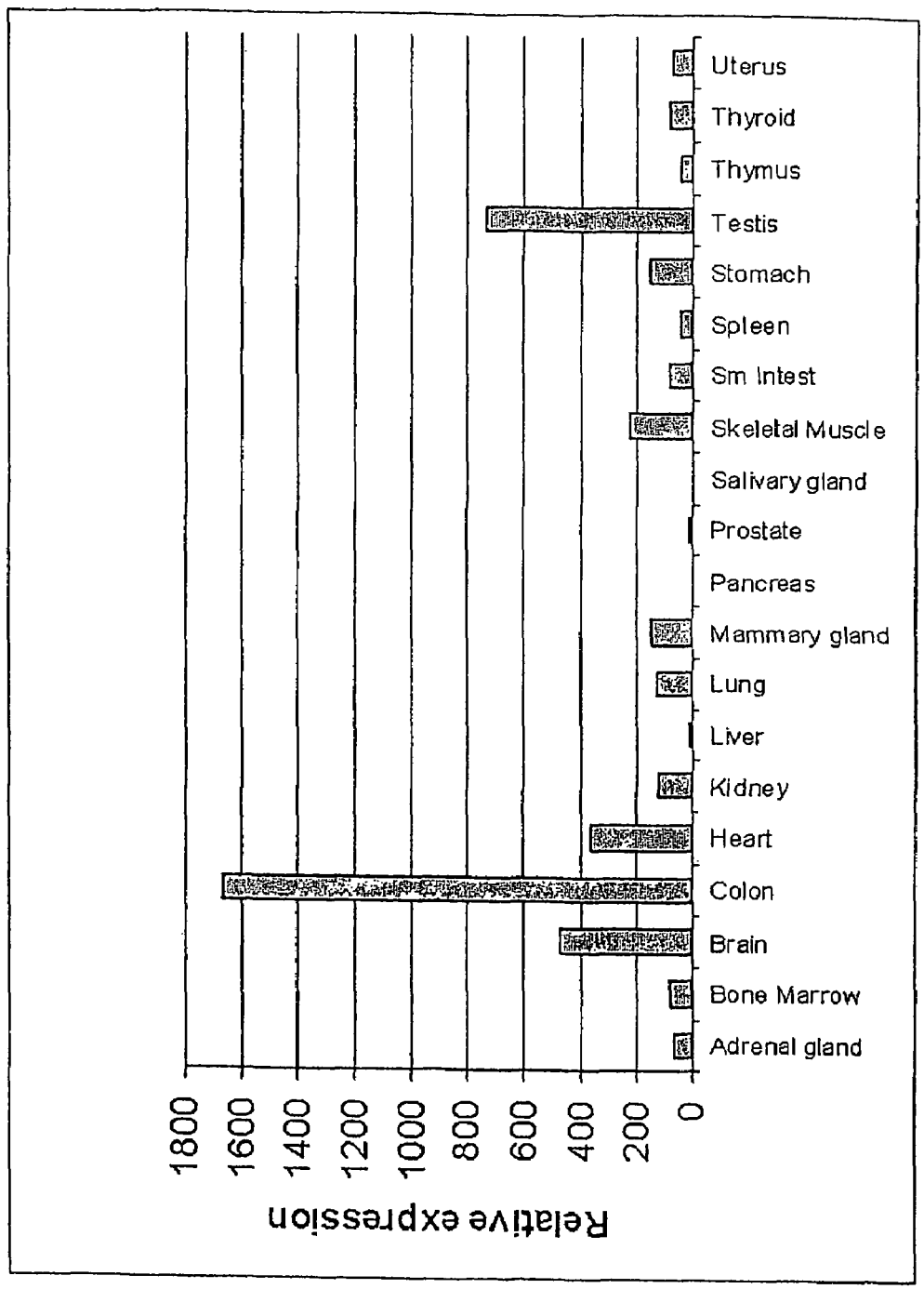
Fig. 16   Relative expression of human PLC delta-1 in various human tissues.

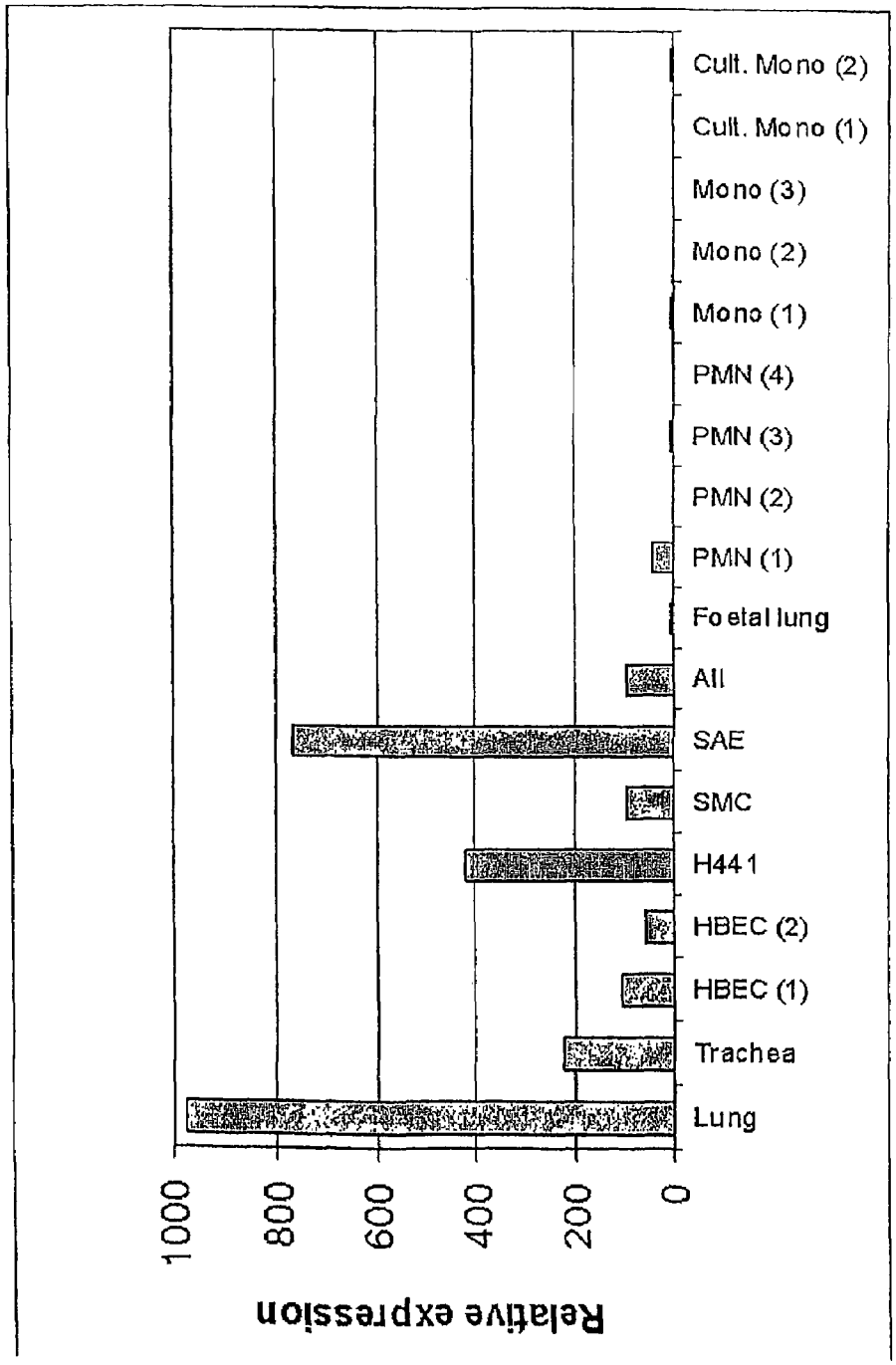

Fig. 17 Relative expression of human PLC delta-1 in various human respiratory tissues and cells.

Key: HBEC=cultured human bronchial epithelial cells; H441=Clara-like cells; SMC=cultured airway smooth muscle cells; SAE= cultured small airway epithelial cells; AII=primary cultured alveolar type II cells; PMN=polymorphonuclear leukocytes; Mono=monocytes; Cult. Mono=cultured monocytes (macrophage-like).

Fig. 1B

```
MGLTEDEDVR AMLRGSRLRK IRSRTWHKER LYRLQEDGLS VWFQRRIPRA PSQHIFFVQH   IEAVREGHQS
EGLRRFGGAF APARCLTIAF KGRRKNLDLA APTAEEAQRW VRGGGDLPAS   YLRAGGSLAC CCYFLSTHTW
IHSYLHRADS NQDSKMSFKE IKSLLRMVNV DMNDMYAYLL   FKECDHSNND RLEGAEIEEF LRRLLKRPEL
EEIFRQYSGE DRVLSAPELL EFLEDQGEEG   ATLARAQQLI QTYELNETAK QHELMTLDGF MMYLLSPEGA
ALDNTHTCVF QDMNQPLAHY   FISSSHNTYL TDSQIGGPSS TEAYVRAFAQ GCRCVELDCW EGPGGEPVIY
HGHTLTSKIL   FRDVVQAVRD HAFTLSPYPV ILSLENHCGL EQQAAMARHL CTILGDMLVT QALDSPNPEE
LPSPEQLKGR VLVKGKKLPA ARSEDGRALS DREEEEEDDE EEEEEVEAAA QRRLVRAGMD   LPGAVGPGCV
LPRHPPATLH PAPNAPQPCQ VSSLSERKAK KLIREAGNSF VRHNARQLTR   VYPLGLRMNS ANYSPQEMWN
SGCQLVALNF QTPGYEMDLN AGRFLVNGQC GYVLKPACLR   QPDSTFDPEY PGPPRTTLSI QVLTAQQLPK
LNAEKPHSIV DPLVRIEIHG VPADCARQET   DYVLNNGFNP RWGQTLQFQL RAPELALVRF VVEDYDATSP
NDFVGQFTLP LSSLKQGYRH   IHLLSKDGAS LSPATLFIQI RIQRS
```

Fig. 19

```
BLASTP - alignment of 101_ext_TR1 against swiss|P51178|PIP6_HUMAN
    This hit is scoring at : 0.0 (expectation value)
    Alignment length (overlap) : 753
    Identities : 48 %
    Scoring matrix : BLOSUM62 (used to infer consensus pattern)
    Database searched : nrdb
Q:       2 GLTEDEDVRAMLRGSRLRKIRSRTWHKERLYRLQEDGLSVWFQ-RRIPRAPSQHIFFVQH
           GL.:DED::A:L:GS:L K::S.:W.:ER.Y:LQED   ::W : R:: R.P...:F ::.
H:      12 GLQDDEDLQALLKGSQLLKVKSSSWRRERFYKLQEDCKTIWQESRKVMRTPESQLFSIED IEAVREGHQSEGLRRFGGAFAPARCLTIAFKGRRKNLDLAAPTAEEAQRWVRGGGDLPAS
           I:.VR GH::EGL.:F.    ... RC.:I.FK.:R..LDL.AP:...:AQ.WV G  .:
           IQEVRMGHRTEGLEKFARDVPEDRCFSIVFKDQRNTLDLIAPSPADAQHWVLGLHKI---

YLRAGGSLACCCYFLSTHTWIHSYLHRADSNQDSKMSFKEIKSLLRMVNVDMNDMYAYLL
           :.. .GS:       .   ... WIHS L.:AD.N:D;KMSFKE:::.L:  :N:..::D.YA  :
           -IHHSGSMD---QRQKLQHWIHSCLRKADKNKDNKMSFKELQNFLKELNIQVDDSYARKI
                                        potential calcium-binding site FKECDHSNNDRLEGAEIEEFLRRLLKRPELEEIFHQYSGEDRVLSAPELLEFLE-DQGEE
           F:ECDHS..D.LE..EIE.F.:.L.:R E::..F : :G....LS..:L:.FL: ..Q EE
           FRECDHSQTDSLEDEEIEAFYKMLTQRVEIDRTFAEAAGPGETLSVDQLVTFLQHQQREE
           Prosite EF-hand calcium-binding domain GATLARAQQLIQTYELNETAKQHELMTLDGFMMYLLSPEGAALDNTHTCVFQDMNQPLAH
           .A  A  A  .LI:.YE :ET.K... MT DGF:MYLLS.:G:A.. .H. V:QDM.QPL:H
           AAGPALALSLIERYEPSETTKAQRQMTKDGFLMYLLSADGSAFSLAHRRVYQDMGQPLSH YFISSSHNTYLTDSQIGGPSSTEAYVRAFAQGCRCVELDCWEGPGGEPVIYHGHTLTSKI
           Y..:SSSHNTYL.:..Q:..GPSSTEAY:RA...:GCRC:ELDCW:GP. EP:IYHG:T.TSKI
           YLVSSSHNTYLLEDQLAGPSSTEAYIRALCKGCRCLELDCWDGPNQEPIIYHGYTFTSKI
               ACT_site                                         ACT_site LFRDVVQAVRDHAFTLSPYPVILSLENHCGLEQQAAMARHLCTILGDMLVTQALDSPNPE
           LF DV::A:RD:AF..SPYPVILSLENHC LEQQ..MARHL .ILG.ML:.:.LD. . .
           LFCDVLRAIRDYAFKASPYPVILSLENHCTLEQQRVMARHLHAILGPMLLNRPLDGVT-N ELPSPEQLKGRVLVKGKKLPAARSXDGRALSDRXXXXXDDXXX---XXXVXAAAQRRLVR
           .LPSPEQLKG::L:KGKKL .. . .G.. .:.......:D...   ...V.:..Q..:  .
           SLPSPEQLKGKILLKGKKLGGLLPPGGEGGPEATVVSDEDEAAEMEDEAVRSRVQHKPKE AGMDLPGAVGPGCVLPRHPPATLHPAPNAPQPC--QVSSLSERKAKKLIREAGNSFVRHN
           : L. .:.. .:. :.     ...:P..P ..  :::S.SE.:A  :L::E:GN.FVRHN
           DKLRLAQELSDMVIYCKSVHFGGFSSPGTPGQAFYEMASFSENRALRLLQESGNGFVRHN ARQLTRVYPLGLRMNSANYSPQEMWNSGCQLVALNFQTPGYEMDLNAGRFLVNGQCGYVL
           . .L:R:YP.G R..:S:NYSP EMWN.GCQ:VALNFQTPG EMD: ..RF  NG.CGYVL
           VGHLSRIYPAGWRTDSSNYSPVEMWNGGCQIVALNFQTPGPEMDVYQDRFQDNGACGYVL KPACLRQPDSTFDP----EYPGPPRTTLSIQVLTAQQLPKLNAEKPHSIVDPLVRIEIHG
           KPA LR.P:.TF:P        :  P  .R..L:I:V::..QQLPK:N..K :SIVDP V.:EIHG
           KPAFLRDPNGTFNPRALAQGPWWARKRLNIRVISGQQLPKVNKNK-NSIVDPKVTVEIHG VPADCARQETDYVLNNGFNPRWGQTLQFQLRAPELALVRFVVEDYDATSPNDFVGQFTLP
           V..D.A.::T . :..NNGFNP W......F::  .P:LAL:RF:VEDYDA:S.NDF:GQ T:P
           VSRDVASRQTAVITNNGFNPWWDTEFAFEVVVPDLALIRFLVEDYDASSKNDFIGQSTIP

LSSLKQGYRHIHLLSKDGASLSPATLFIQIRIQ   743
```

Fig. 19 (cont'd)

```
        L:SLKQGYRH:HL:SK:G . ..ATLF::I.:Q
        LNSLKQGYRHVHLMSKNGDQHPSATLFVKISLQ       755
Phosphatidylinositol-specific phospholipase X BLOCKS BLOCKS search results
AC#         Description                                    Strength   Score
BL50007A      Phosphatidylinositol-specific phospholipase X    1625    1780
   AA#    296 LAHYFISSSHNTYLTdsQIGGPSSTEAYvRAfaQGCRCVELDCWeG
BL50007D      Phosphatidylinositol-specific phospholipase X    1492    1658
   AA#    532 HNaRQLTRVYPlGLRMnSaNYSPQEMWNsGCQLVALNFQTPG
BL50007B      Phosphatidylinositol-specific phospholipase X    1403    1616
   AA#    355 TSKILFRDVVQAvRDHAFtlSPYPVILSLENHCgLEQQ
BL50007C      Phosphatidylinositol-specific phospholipase X    1240    1391
   AA#    420 LPSPEQLKGRvLVKGKK
BL50007E      Phosphatidylinositol-specific phospholipase X    1216    1340
   AA#    694 YDAtSpNDFVGQFTLPLSSLKQGYRHIHLLSKdGasL
```

Fig. 20

HMMPFAM - alignment of 101_ext_TR1 against pfam|hmm|PI-PLC-X
    Phosphatidylinositol-specific phospholipase
    This hit is scoring at : 262.2; Expect = 6.7e-75
    Scoring matrix : BLOSUM62 (used to infer consensus pattern)
Q:     292 DMNQPLAHYFISSSHNTYLTDSQIGGPSSTEAYVRAFAQGCRCVELDCWEG-PGGEPVIY
           DM: PL:HYFISSSHNTYLT..Q: G.SS.E:Y :.. .GCRCVELDCW:G P..EP:IY
H:       1 dmsiPLsHYfisSshntYLtgkQlwGkssvesYrqqLdaGcRcvELDcwdGkpddepiIy HGHTLTSKILFRDVVQAVRDHAFT-LSPYPVILSLENHCGLE-QQAAMARHLCTILGDML
           HGHTLT :I .:DV::A::D.AF. .SPYPVILSLENHC. : QQ..MA::. .I.GDML
           HGhtltleiklkdVleaIkdfafkPtSpyPvIlSlenHcnsddqQrkmakyfkeiFgdmL VTQA-LDSpNPEE----LPSPEQLKGRVLVKGKK        437
           :T:. LDS  ..E    LPS :.L:G::L:K.KK
           ltkPtlds.lttepglpLPslkdlrgKILLknkk        153

Fig. 21

HMMPFAM - alignment of 101_ext_TR1 against pfam|hmm|PI-PLC-Y
    Phosphatidylinositol-specific phospholipase
    This hit is scoring at : 181.9; Expect = 1e-50
    Scoring matrix : BLOSUM62 (used to infer consensus pattern)
Q:    510 QVSSLSER--KAKKLIREAGNSFVRHNARQLTRVYPLGLRMNSANYSPQEMWNSGCQLVA
            ::SS.SER  KAKKL::E:   .FV::N.RQL:RVYP G.R::S:N:.PQ .WN:GCQ:VA
H:     29 eisSFsErkvkakkllkespvefVkyNkrqLsRvYPkGtRvDSSNfmPqvfWnaGCQmVA LNFQTPGYEMDLNAGRFLVNGQ-------CGYVLKPACLR        600
            LNFQT....M.:N G.F .NG          .GY:LKP. LR
            LNfQTsDlpmqiNdGmFeyNggqPdGsfksGYlLKPeflR        128

Fig. 22

```
HMMPFAM - alignment of 101_ext_TR1 against pfam|hmm|C2
    C2 domain
    This hit is scoring at : 89.5; Expect = 6.7e-23
    Scoring matrix : BLOSUM62 (used to infer consensus pattern)
Q:   618 LSIQVLTAQQLPKLNAekPHS-IVDPLVRIEIHGVPADCARQETDYVLNN-GFNPRWG-Q
         L::.V:.A:.LPK:.     :. : DP.V::.: G ..D..: :T..V .. G.NP W. :
H:     1 LtVtvieArnLpkmDk..vngrlsDPYVkvsllgdkkdlkkfkTkvvkktNGLNPvWneE TLQFQ-LRAPELAL--VRFVVEDYDATSPNDFVGQFT        708
         T. F: : .PELA   :RF.V D D. S :DF:GQ.T
         tFvFekvplpelasktLrfaVyDedrfsrdDfiGqvt         95
```

REGULATION OF HUMAN PLC DELTA-1

This application is 371 National Stage application of PCT application PCT/EP01/06087 filed May 29, 2001, which was published in English under PCT Article 21(2) on Dec. 6, 2001, which claims the benefit of U.S. provisional application Ser. No. 60/207,277 filed May 30, 2000 and Ser. No. 60/278,742 filed Mar. 27, 2001.

These applications are incorporated herein by reference in their entireties.

TECHNICAL FIELD OF THE INVENTION

The invention relates to the regulation of human PLC delta-1 activity for therapeutic effects.

BACKGROUND OF THE INVENTION

Phospholipase C

Phospholipase C (PLC) belongs to a family of enzymes, also known as disulfide isomerases, which play a very important role in transmembrane signal transduction (see U.S. Pat. No. 5,587,306). Many extracellular signaling molecules including hormones, growth factors, neurotransmitters, and immunoglobulins bind to their respective cell surface receptors and activate PLCs. The role of an activated PLC is to catalyze the hydrolysis of phosphatidylinositol-4, 5-bisphosphate (PIP2), a minor component of the plasma membrane to produce diacylglycerol and inositol 1,4,5-trisphosphate (IP3).

In their respective biochemical pathways, IP3 and diacylglycerol serve as second messengers and trigger a series of intracellular responses. IP3 induces the release of $Ca^{++}$ from internal cellular storage, and diacylglycerol activates protein kinase C (PKC). Both pathways are part of transmembrane signal transduction mechanisms which regulate cellular processes which include secretion, neural activity, metabolism, and proliferation. For example, interleukin 4 receptor signaling in human monocytes involves activation of PLC (Ho et al., *J. Exp. Med.* 180, 1457–69, 1994).

Several distinct isoforms of PLC have been identified and are categorized as PLC-beta, PLC-gamma, and PLC-delta. Subtypes are designated by adding Arabic numbers after the Greek letters, e.g. PLC-beta-1. PLCs have a molecular mass of 62–68 kDa, and their amino acid sequences show two regions of significant similarity. The first region designated X has about 170 amino acids, and the second or Y region contains about 260 amino acids.

The Mechanism of G Protein-Mediated Transmembrane Signaling

The activation of a particular PLC is mediated by a guanine nucleotide binding-regulatory protein (G-protein) or by the intrinsic tyrosine kinase activity of cell surface receptors. Many plasma membrane-bound receptors, including the hormone receptors, activate the cell's G proteins. Each G protein can act as a molecular switch turning on one or more membrane-bound effectors such as adenylate cyclase, ion channels, or phospholipase C.

G proteins are heterotrimers with alpha, beta, and gamma subunits. Inactive G proteins have guanine diphosphate (GDP) molecule bound tightly to their alpha subunit. When a G-protein linked receptor binds an extracellular ligand, such as a hormone, the hormone-receptor complex causes dissociation of GDP from the alpha-subunit. Immediately thereafter, GTP molecules fill the site, and activity of the alpha subunit's intrinsic ATPase causes dissociation of the G protein from the hormone-receptor complex. Simultaneously, GTP binding reduces the affinities between the alpha-, beta- and gamma-subunits and frees the beta-gamma complex. In some systems, the beta-gamma complex then activates PLC beta-2 (Katz et al., *Nature* 360, 686–89, 1992).

Phospholipase Isoforms and Their Cellular Activity

The catalytic activities of the three isoforms of PLC are dependent upon $Ca^{++}$. It has been suggested that the binding sites for $Ca^{++}$ in the PLCs are located in the Y-region, one of two conserved regions. The hydrolysis of common inositol-containing phospholipids—phosphatidylinositol (PI), phosphatidylinositol 4-monophosphate (PIP), and phosphatidylinositol 4,5-bisphosphate (PIP2) by any of the isoforms yields cyclic and noncyclic inositol phosphates. A large number of hormones and related molecules are known to activate phospholipases.

PLC-Beta Isoforms

Both beta-1 and beta-2 isoforms of PLC are activated by certain subtypes of G-proteins and related G protein alpha-subunits during the transduction of signals from cell surface receptors to PLC. There may be two distinct types of G proteins, one pertussis toxin sensitive and the other insensitive, which activate the beta-1 isoform. Katz et al., supra, suggest that the beta subunit of the G protein may also activate PLC beta-1. The activation of PLCs is achieved by increasing their intrinsic activity rather than by reducing the PLC's requirement of $Ca^{++}$ in the cytosol.

PLC-Gamma Isoforms

The PLC gamma-1 isoform is mainly phosphorylated and activated by growth factor receptors belonging to the tyrosine kinase family. In addition, the growth factor receptors associate with the gamma-1 isoform before any tyrosine phosphorylation occurs. The major sites of tyrosine phosphorylation by the receptors for epidermal growth factor (EGF), platelet-derived growth factor (PDGF), and nerve growth factor (NGF) appear to be Tyr-771, Tyr-783, and Tyr-1254 in the PLC amino acid sequence. Phosphorylation of Tyr-783 in the gamma-1 isoform by the receptor tyrosine kinase is essential for the activation of the gamma-1 isoform.

Other evidence suggests that non-receptor protein tyrosine kinases can also phosphorylate and activate the gamma-1 isoform in response to certain cell surface receptors in leukocytes. For instance, the T cell antigen receptors complex can recognize antigens and transduce signals across the plasma membrane. Likewise, it appears that non-receptor protein tyrosine kinases can activate the gamma-2 isoform.

Evidence suggests that the activation of the gamma-2 isoform is necessary for stimulation of phospholipase D by platelet-derived growth factor (Yeo et al., *J. Biol. Chem.* 269, 27823–26, 1994). Other evidence suggests that B cell surface antigen CD20 is associated with tyrosine and serine kinases and involved in tyrosine phosphorylation and activation of the gamma-1 and gamma-2 isoforms (Deans et al., *J. Immunol.* 151, 4494–504, 1993).

Growth factor-induced activation of PLCs appears to be independent of G-protein mediation. Marrero et al., *J. Biol. Chem.* 269, 10935–39, 1994), however, reported an exception in rat aortic vascular smooth muscle cells where PLC-gamma-1 was activated by a G-protein-coupled receptor.

PLC-Delta

Neither receptors nor transducers of the PLC-delta isoforms have been identified.

Inhibition of PLCs by Protein Kinases

Evidence suggests that the activation of protein kinases may serve as negative feed back signals and attenuate receptor-coupled PLC activity including the magnitude and duration in certain types of cells. For instance, the phosphorylation of Thr-654 in the EGF receptors by protein kinase prevents activation of the gamma-1 isoform by reducing the capacity of the receptor tyrosine kinase to phosphorylate the gamma-1 isoform. In addition, PKC activators such as cAMP and phorbol 12-myristate 13-acetate (PMA) attenuate the PIP2 hydrolysis induced by T cell antigen receptors. Likewise, the beta-1 isoform of PLC appears to be regulated by PKC in certain cells.

Effects of the Second Messengers and Calcium Cations

Inositol Trisphosphate

Once activated, PLCs catalyze the hydrolysis of phosphatidylinositol-4,5-bisphosphate (PIP2) to produce diacylglycerol and inositol 1,4,5-trisphosphate (IP3), all of which serve as second messengers. Inositol trisphosphate releases $Ca^{++}$ from intracellular stores and increases the influx of $Ca^{++}$ from the extracellular fluid. $Ca^{++}$ directly regulates target enzymes and indirectly affects other enzymes by functioning as a second messenger and interacting with $Ca^{++}$-binding proteins, such as troponin C and calmodulin.

Deactivation of the inositol trisphosphate pathway is achieved by active transport of $Ca^{++}$ into cells and extrusion of ions by plasma membrane-bound, $Ca^{++}$-pumping ATPases. Likewise, sequential phosphorylation degrades inositol trisphosphate.

Diacylglycerol

Diacylglycerol, a product of the hydrolysis by PLCs, acts as a second messenger by activating protein kinase C. After protein kinase C binds to diacylglycerol, the requirement of $Ca^{++}$ by protein kinase C decreases to the level of free $Ca^{++}$ found in the cytosol. Activated protein kinase C phosphorylates a great number of intracellular proteins. The termination of the diacylglycerol effect is achieved by enzymatic recycling to form phosphatidylinositol. Alternatively, a diacylglycerol lipase breaks down diacylglycerol.

PLC and Diseases

Evidence indicates that a high percentage of primary human mammary carcinomas concomitantly show increased levels of receptor EGF and PLC-gamma-1. Likewise, studies on spontaneous hypertensive rats have suggested that one of the main causes for the hypertension is an abnormal activation of PLC-delta-1 resulting from point mutations in the X and Y regions of the PLC amino acid sequence.

The biology of PLC is reviewed, inter alia, in Isselbacher et al., HARRISON'S PRINCIPLES OF INTERNAL MEDICINE, McGraw-Hill, New York City, 1994; Kuruvilla et al., *J. Immunol.* 151, 637–48, 1993; and Rhee & Choi, *J. Biol. Chem.* 267, 12393–96, 1994.

Because of the important role of PLC enzymes, there is a need in the art to identify additional members of this enzyme family which can be regulated to provide therapeutic effects.

SUMMARY OF THE INVENTION

It is an object of the invention to provide reagents and methods of regulating a human PLC delta-1. This and other objects of the invention are provided by one or more of the embodiments described below.

One embodiment of the invention is a PLC delta-1 polypeptide comprising an amino acid sequence selected from the group consisting of:

amino acid sequences which are at least about 50% identical to the amino acid sequence shown in SEQ ID NO: 2;

the amino acid sequence shown in SEQ ID NO: 2;

amino acid sequences which are at least about 50% identical to the amino acid sequence shown in SEQ ID NO: 4;

the amino acid sequence shown in SEQ ID NO:4;

amino acid sequences which are at least about 50% identical to the amino acid sequence shown in SEQ ID NO: 9;

the amino acid sequence shown in SEQ ID NO: 9;

amino acid sequences which are at least about 50% identical to the amino acid sequence shown in SEQ ID NO: 13; and the amino acid sequence shown in SEQ ID NO: 13.

Yet another embodiment of the invention is a method of screening for agents which decrease extracellular matrix degradation. A test compound is contacted with a PLC delta-1 polypeptide comprising an amino acid sequence selected from the group consisting of:

amino acid sequences which are at least about 50% identical to the amino acid sequence shown in SEQ ID NO: 2;

the amino acid sequence shown in SEQ ID NO: 2;

amino acid sequences which are at least about 50% identical to the amino acid sequence shown in SEQ ID NO: 4;

the amino acid sequence shown in SEQ ID NO:4;

amino acid sequences which are at least about 50% identical to the amino acid sequence shown in SEQ ID NO: 9;

the amino acid sequence shown in SEQ ID NO: 9;

amino acid sequences which are at least about 50% identical to the amino acid sequence shown in SEQ ID NO: 13; and the amino acid sequence shown in SEQ ID NO: 13.

Binding between the test compound and the PLC delta-1 polypeptide is detected. A test compound which binds to the PLC delta-1 polypeptide is thereby identified as a potential agent for decreasing extracellular matrix degradation. The agent can work by decreasing the activity of the PLC delta-1.

Another embodiment of the invention is a method of screening for agents which decrease extracellular matrix degradation. A test compound is contacted with a polynucleotide encoding a PLC delta-1 polypeptide, wherein the polynucleotide comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 3;

the nucleotide sequence shown in SEQ ID NO: 3;

nucleotide sequences which are at least about 50% identical to the nucleotide sequence shown in SEQ ID NO: 5;

the nucleotide sequence shown in SEQ ID NO:5;

nucleotide sequences which are at least about 50% identical to the nucleotide sequence shown in SEQ ID NO: 6;

the nucleotide sequence shown in SEQ ID NO: 6;

nucleotide sequences which are at least about 50% identical to the nucleotide sequence shown in SEQ ID NO: 7;

the nucleotide sequence shown in SEQ ID NO: 7;

nucleotide sequences which are at least about 50% identical to the nucleotide sequence shown in SEQ ID NO: 8;
the nucleotide sequence shown in SEQ ID NO:8;
nucleotide sequences which are at least about 50% identical to the nucleotide sequence shown in SEQ ID NO: 10; and
the nucleotide sequence shown in SEQ ID NO: 10.

Binding of the test compound to the polynucleotide is detected. A test compound which binds to the polynucleotide is identified as a potential agent for decreasing extracellular matrix degradation. The agent can work by decreasing the amount of the PLC delta-1 through interacting with the PLC delta-1 mRNA.

Another embodiment of the invention is a method of screening for agents which regulate extracellular matrix degradation. A test compound is contacted with a PLC delta-1 polypeptide comprising an amino acid sequence selected from the group consisting of:
amino acid sequences which are at least about 50% identical to the amino acid sequence shown in SEQ ID NO: 2;
the amino acid sequence shown in SEQ ID NO: 2;
amino acid sequences which are at least about 50% identical to the amino acid sequence shown in SEQ ID NO: 4;
the amino acid sequence shown in SEQ ID NO:4;
amino acid sequences which are at least about 50% identical to the amino acid sequence shown in SEQ ID NO: 9;
the amino acid sequence shown in SEQ ID NO: 9;
amino acid sequences which are at least about 50% identical to the amino acid sequence shown in SEQ ID NO: 13; and
the amino acid sequence shown in SEQ ID NO: 13.

A PLC delta-1 activity of the polypeptide is detected. A test compound which increases PLC delta-1 activity of the polypeptide relative to PLC delta-1 activity in the absence of the test compound is thereby identified as a potential agent for increasing extracellular matrix degradation. A test compound which decreases PLC delta-1 activity of the polypeptide relative to PLC delta-1 activity in the absence of the test compound is thereby identified as a potential agent for decreasing extracellular matrix degradation.

Even another embodiment of the invention is a method of screening for agents which decrease extracellular matrix degradation. A test compound is contacted with a PLC delta-1 product of a polynucleotide which comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 3;
the nucleotide sequence shown in SEQ ID NO: 3;
nucleotide sequences which are at least about 50% identical to the nucleotide sequence shown in SEQ ID NO: 5;
the nucleotide sequence shown in SEQ ID NO:5;
nucleotide sequences which are at least about 50% identical to the nucleotide sequence shown in SEQ ID NO: 6;
the nucleotide sequence shown in SEQ ID NO: 6;
nucleotide sequences which are at least about 50% identical to the nucleotide sequence shown in SEQ ID NO: 7;
the nucleotide sequence shown in SEQ ID NO: 7;
nucleotide sequences which are at least about 50% identical to the nucleotide sequence shown in SEQ ID NO: 8;
the nucleotide sequence shown in SEQ ID NO:8;
nucleotide sequences which are at least about 50% identical to the nucleotide sequence shown in SEQ ID NO: 10; and
the nucleotide sequence shown in SEQ ID NO: 10.

Binding of the test compound to the PLC delta-1 product is detected. A test compound which binds to the PLC delta-1 product is thereby identified as a potential agent for decreasing extracellular matrix degradation.

Still another embodiment of the invention is a method of reducing extracellular matrix degradation. A cell is contacted with a reagent which specifically binds to a polynucleotide encoding a PLC delta-1 polypeptide or the product encoded by the polynucleotide, wherein the polynucleotide comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 3;
the nucleotide sequence shown in SEQ ID NO: 3;
nucleotide sequences which are at least about 50% identical to the nucleotide sequence shown in SEQ ID NO: 5;
the nucleotide sequence shown in SEQ ID NO:5;
nucleotide sequences which are at least about 50% identical to the nucleotide sequence shown in SEQ ID NO: 6;
the nucleotide sequence shown in SEQ ID NO: 6;
nucleotide sequences which are at least about 50% identical to the nucleotide sequence shown in SEQ ID NO: 7;
the nucleotide sequence shown in SEQ ID NO: 7;
nucleotide sequences which are at least about 50% identical to the nucleotide sequence shown in SEQ ID NO: 8;
the nucleotide sequence shown in SEQ ID NO:8;
nucleotide sequences which are at least about 50% identical to the nucleotide sequence shown in SEQ ID NO: 10; and
the nucleotide sequence shown in SEQ ID NO: 10.

PLC delta-1 activity in the cell is thereby decreased.

The invention thus provides reagents and methods for regulating human PLC delta-1 which can be used inter alia, to treat COPD, congestive heart failure, hypertension, and cancer, and a variety of conditions in which signal transduction is impaired.

BRIEF DESCRIPTION OF THE DRAWINGS

FIG. 1 shows the DNA-sequence encoding a PLC delta-1 polypeptide.

FIG. 2 shows the amino acid sequence deduced from the DNA-sequence of FIG. 1.

FIG. 3 shows the DNA-sequence encoding a PLC delta-1 polypeptide.

FIG. 4 shows the amino acid sequence deduced from the DNA-sequence of FIG. 3.

FIG. 5 shows the DNA-sequence encoding a PLC delta-1 polypeptide.

FIG. 6 shows the DNA-sequence encoding a PLC delta-1 polypeptide.

FIG. 7 shows the DNA-sequence encoding a PLC delta-1 polypeptide.

FIG. 8 shows the DNA-sequence encoding a PLC delta-1 polypeptide.

FIG. 9 shows the amino acid sequecne of a PLC delta-1 polypeptide.

FIG. 10 shows the DNA-sequence encoding a PLC delta-1 polypeptide.

FIG. 11 shows the amino acid sequence of the rat protein identified with SwissProt Accession No. P10688.

FIG. 12 shows the amino acid sequence of the rat protein identified with SwissProt Accsion No. P10688.

FIG. 13 shows the BLASTP alignment of the PLC delta-1 polypeptide of FIG. 4 with the rat protein identified with SwissProt Accession No. P10688 of FIG. 11. The pleckstrin homology domain is indicated in bold.

FIG. 14 shows the HMMPFAM alignment of the PLC delta-1 polypeptide of FIG. 4 with pfam?hmm?PH of FIG. 12. PFAM is a large collection of multiple sequence alignments and hidden Markov models (HMM) covering many common protein domains.

FIG. 15 shows the tBLASTn alignment of the rat protein identified with SwissProt Accession No. P10688 of FIG. 12 with the PLC delta-1 polypeptide of FIG. 9.

FIG. 16 shows the relative expression of human PLC delta-1 in various human tissues.

FIG. 17 shows the relative expression of human PLC delta-1 in various human respiratory tissues and cells.

FIG. 18 shows the amino acid sequence deduced from the DNA-sequence of FIG. 10.

FIG. 19 shows the BLAST alignment of 101_ext_TR1 against swiss/P51178/PIP6_HUMAN.

FIG. 20 shows the HMMPFAM alignment of 101_ext_TR1 against pfam/hmm/PI-PLC-X.

FIG. 21 shows the HMMPFAM alignment of 101_ext_TR1 against pfam/hmm/PI-PLC-Y.

FIG. 22 shows the HMMPFAM alignment of 101_ext_TR1 against pfam/hmm/C2.

DETAILED DESCRIPTION OF THE INVENTION

The invention relates to an isolated polynucleotide encoding a PLC delta-1 polypeptide and being selected from the group consisting of:
a) a polynucleotide encoding a PLC delta-1 polypeptide comprising an amino acid sequence selected from the group consisting of:
   amino acid sequences which are at least about 50% identical to the amino acid sequence shown in SEQ ID NO: 2;
   the amino acid sequence shown in SEQ ID NO: 2;
   amino acid sequences which are at least about 50% identical to the amino acid sequence shown in SEQ ID NO: 4;
   the amino acid sequence shown in SEQ ID NO:4;
   amino acid sequences which are at least about 50% identical to the amino acid sequence shown in SEQ ID NO: 9;
   the amino acid sequence shown in SEQ ID NO: 9;
   amino acid sequences which are at least about 50% identical to the amino acid sequence shown in SEQ ID NO: 13; and
   the amino acid sequence shown in SEQ ID NO: 13.
b) a polynucleotide comprising the sequence of SEQ ID NOS: 1, 3, 5, 6, 7, 8 or 10;
c) a polynucleotide which hybridizes under stringent conditions to a polynucleotide specified in (a) and (b);
d) a polynucleotide the sequence of which deviates from the polynucleotide sequences specified in (a) to (c) due to the degeneration of the genetic code; and
e) a polynucleotide which represents a fragment, derivative or allelic variation of a polynucleotide sequence specified in (a) to (d).

Furthermore, it has been discovered by the present applicant that a novel 1-phosphatidylinositol-4,5-bisphosphate phosphodiesterase delta 1 (PLC delta-1), particularly a human PLC delta-1, is a discovery of the present invention. Human PLC delta-1 is 43% identical over 117 amino acids to the rat protein identified with SwissProt Accession No. P10688 (SEQ ID NO:11) and annotated as a 1-phosphatidylinositol-4,5-bisphosphate phosphodiesterase delta 1 (FIG. 1). The SwissProt entry of P10688 (SEQ ID NO:11) bears the following annotations: "Hydrolase; Lipid degradation; Transducer; Calcium-binding." The alignment of human PLC delta-1 with this rat homolog covers the pleckstrin homology (PH) domain, which is responsible for high affinity binding to PI3 or PIP2. Human PLC delta-1 thus is likely to be useful for the same purposes as previously identified PLC delta-1 proteins.

Polypeptides

PLC delta-1 polypeptides according to the invention comprise at least 25, 50, or 100 contiguous amino acids of SEQ ID NO:2 or a biologically active variant thereof, as defined below. A PLC delta-1 polypeptide of the invention therefore can be a portion of a PLC delta-1 molecule, a full-length PLC delta-1 molecule, or a fusion protein comprising all or a portion of a PLC delta-1 molecule.

Biologically Active Variants

PLC delta-1 variants which are biologically active, e.g., retain a PLC delta-1 activity, also are PLC delta-1 polypeptides. Preferably, naturally or non-naturally occurring PLC delta-1 variants have amino acid sequences which are at least about 50, preferably about 75, 90, 96, or 98% identical to an amino acid sequence shown in SEQ ID NOS:2, 4, 9 or 13. Percent identity between a putative PLC delta-1 variant and an amino acid sequence of SEQ ID NO:2, 4, or 9 is determined using the Needleman and Wunsch algorithm (Needleman and Wunsch, J.Mol. Biol. 48; 443–453, 1970) with the substitution-matrix BLOSUM62 (S. Henikof Proc. Natl. Acad. Sci. USA 89:10915–10919, 1992) using a gap creation penalty" of 8 and a gap extension penalty of 2.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity can be found using computer programs well known in the art, such as DNASTAR software. Whether an amino acid change results in a biologically active PLC delta-1 polypeptide can readily be determined by assaying for fibronectin binding or for PLC delta-1 activity, as is known in the art and described, for example, in the specific examples below.

Fusion Proteins

Fusion proteins are useful for generating antibodies against PLC delta-1 amino acid sequences and for use in various assay systems. For example, fusion proteins can be used to identify proteins which interact with portions of a PLC delta-1 polypeptide, including its active site and fibronectin domains. Methods such as protein affinity chromatography or library-based assays for protein-protein interactions, such as the yeast two-hybrid or phage display systems, can be used for this purpose. Such methods are well known in the art and also can be used as drug screens.

A PLC delta-1 fusion protein comprises two protein segments fused together by means of a peptide bond. Contiguous amino acids for use in a fusion protein can be selected from the amino acid sequences shown in SEQ ID NO:2, 4, 9 or 13 or from a biologically active variant thereof, such as those described above. For example, the first protein segment can comprise at least 25, 50, or 100 contiguous amino acids of SEQ ID NO:2 or a biologically active variant thereof Preferably, a fusion protein comprises the active site of the PLC delta-1 or the pleckstrin domain shown in FIG. 1. The first protein segment also can comprise full-length PLC delta-1.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP) and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the PLC delta-1 polypeptide-encoding sequence and the heterologous protein sequence, so that the PLC delta-1 polypeptide can be cleaved and purified away from the heterologous moiety.

A fusion protein can be synthesized chemically, as is known in the art. Preferably, a fusion protein is produced by covalently linking two protein segments or by standard procedures in the art of molecular biology. Recombinant DNA methods can be used to prepare fusion proteins, for example, by making a DNA construct which comprises PLC delta-1 coding sequences disclosed herein in proper reading frame with nucleotides encoding the second protein segment and expressing the DNA construct in a host cell, as is known in the art. Many kits for constructing fusion proteins are available from companies such as Promega Corporation Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human PLC delta-1 can be obtained using PLC delta-1 polynucleotides (described below) to make suitable probes or primers to screening cDNA expression libraries from other species, such as mice, monkeys, or yeast, identifying cDNAs which encode homologs of PLC delta-1, and expressing the cDNAs as is known in the art.

Polynucleotides

A PLC delta-1 polynucleotide can be single- or double-stranded and comprises a coding sequence or the complement of a coding sequence for a PLC delta-1 polypeptide. A nucleotide sequence encoding the human PLC delta-1 polypeptide shown in SEQ ID NO:13 is shown in SEQ ID NO:10.

Degenerate nucleotide sequences encoding human PLC delta-1 polypeptides, as well as homologous nucleotide sequences which are at least about 50, preferably about 75, 90, 96, or 98% identical to the PLC delta-1 coding sequences nucleotide sequence shown in SEQ ID NO:10 also are PLC delta-1 polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of PLC delta-1 polynucleotides which encode biologically active PLC delta-1 polypeptides also are PLC delta-1 polynucleotides.

Identification of Variants and Homologs

Variants and homologs of the PLC delta-1 polynucleotides disclosed above also are PLC delta-1 polynucleotides. Typically, homologous PLC delta-1 polynucleotide sequences can be identified by hybridization of candidate polynucleotides to known PLC delta-1 polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the PLC delta-1 polynucleotides disclosed herein can be identified by making suitable probes or primers and screening cDNA expression libraries from other species, such as mice, monkeys, or yeast. Human variants of PLC delta-1 polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human PLC delta-1 polynucleotides or PLC delta-1 polynucleotides of other species can therefore be identified, for example, by hybridizing a putative homologous PLC delta-1 polynucleotide with a polynucleotide having a nucleotide sequence of SEQ ID NO:1, 5, or 7 or the complement of SEQ ID NO:3 to form a test hybrid. The melting temperature of the test hybrid is compared with the melting temperature of a hybrid comprising PLC delta-1 polynucleotides having perfectly complementary nucleotide sequences, and the number or percent of basepair mismatches within the test hybrid is calculated.

Nucleotide sequences which hybridize to PLC delta-1 polynucleotides or their complements following stringent hybridization and/or wash conditions are also PLC delta-1 polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a PLC delta-1 polynucleotide having a coding sequence disclosed herein and a polynucleotide sequence which is at least about 50, preferably about 75, 90, 96, or 98% identical to that nucleotide sequence can be calculated, for example, using the equation of Bolton and McCarthy, *Proc. Natl. Acad. Sci. U.S.A.* 48, 1390 (1962):

$$T_m = 81.5°\text{ C.} - 16.6(\log_{10}[\text{Na}^+]) + 0.41(\% \text{ G+C}) - 0.63(\% \text{ formamide}) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring PLC delta-1 polynucleotide can be isolated free of other cellular components such as membrane components, proteins, and lipids. Polynucleotides can be made by a cell and isolated using standard nucleic acid purification techniques, synthesized using an amplification technique, such as the polymerase chain reaction (PCR), or synthesized using an automatic synthesizer. Methods for isolating polynucleotides are routine and are known in the art. Any such technique for obtaining a polynucleotide can be used to obtain isolated PLC delta-1 polynucleotides. For example, restriction enzymes and probes can be used to isolate polynucleotide fragments which comprise PLC delta-1 nucleotide sequences. Isolated polynucleotides are in preparations which are free or at least 70, 80, or 90% free of other molecules.

PLC delta-1 cDNA molecules can be made with standard molecular biology techniques, using PLC delta-1 mRNA as a template. PLC delta-1 cDNA molecules can thereafter be replicated using molecular biology techniques known in the art and disclosed in manuals such as Sambrook et al. (1989). An amplification technique, such as PCR, can be used to obtain additional copies of PLC delta-1 polynucleotides, using either human genomic DNA or cDNA as a template.

Alternatively, synthetic chemistry techniques can be used to synthesize PLC delta-1 polynucleotides. The degeneracy of the genetic code allows alternate nucleotide sequences to be synthesized which will encode a PLC delta-1 polypeptide having, for example, the amino acid sequence shown in SEQ ID NO:2 or 13 or a biologically active variant thereof.

Obtaining Full-Length Polynucleotides

The partial sequences of SEQ ID NOS:1, 3, and 5–8 or their complements can be used to identify the corresponding full length gene from which they were derived. The partial sequences can be nick-translated or end-labeled with $^{32}$P using polynucleotide kinase using labeling methods known to those with skill in the art (BASIC METHODS IN MOLECULAR BIOLOGY, Davis et al., eds., Elsevier Press, N.Y., 1986). A lambda library prepared from human tissue can be directly screened with the labeled sequences of interest or the library can be converted en masse to pBluescript (Stratagene Cloning Systems, La Jolla, Calif. 92037) to facilitate bacterial colony screening (see Sambrook et al., 1989, pg. 1.20).

Both methods are well known in the art. Briefly, filters with bacterial colonies containing the library in pBluescript or bacterial lawns containing lambda plaques are denatured, and the DNA is fixed to the filters. The filters are hybridized with the labeled probe using hybridization conditions described by Davis et al., 1986. The partial sequences, cloned into lambda or pBluescript, can be used as positive controls to assess background binding and to adjust the hybridization and washing stringencies necessary for accurate clone identification. The resulting autoradiograms are compared to duplicate plates of colonies or plaques; each exposed spot corresponds to a positive colony or plaque. The colonies or plaques are selected and expanded, and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined, for example after exonuclease m digestion (McCombie et al., *Methods* 3, 33–40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

Various PCR-based methods can be used to extend the nucleic acid sequences encoding the disclosed portions of human PLC delta-1 to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations are used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991. Additionally, PCR, nested primers, and PROMOTERFINDER libraries (CLONTECH, Palo Alto, Calif.) can be used to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T)

library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

PLC delta-1 polypeptides can be obtained, for example, by purification from human cells, by expression of PLC delta-1 polynucleotides, or by direct chemical synthesis.

Protein Purification

PLC delta-1 polypeptides can be purified from cells, including cells which have been transfected with PLC delta-1 expression constructs. Senescent fibroblasts, colon, and brain anaplastic oligodendroglioma are especially useful sources of PLC delta-1 polypeptides. A purified PLC delta-1 polypeptide is separated from other compounds which normally associate with the PLC delta-1 polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified PLC delta-1 polypeptides is at least 80% pure; preferably, the preparations are 90%, 95%, or 99% pure. Purity of the preparations can be assessed by any means known in the art, such as SDS-polyacrylamide gel electrophoresis. Enzymatic activity of the purified preparations can be assayed, for example, as described in the specific examples, below.

Expression of Polynucleotides

To express a PLC delta-1 polypeptide, a PLC delta-1 polynucleotide can be inserted into an expression vector which contains the necessary elements for the transcription and translation of the inserted coding sequence. Methods which are well known to those skilled in the art can be used to construct expression vectors containing sequences encoding PLC delta-1 polypeptides and appropriate transcriptional and translational control elements. These methods include in vitro recombinant DNA techniques, synthetic techniques, and in vivo genetic recombination. Such techniques are described, for example, in Sambrook et al. (1989) and Ausubel et al., CURRENT PROTOCOLS IN MOLECULAR BIOLOGY, John Wiley & Sons, New York, N.Y, 1989.

A variety of expression vector/host systems can be utilized to contain and express sequences encoding a PLC delta-1 polypeptide. These include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a PLC delta-1 polypeptide, vectors based on SV40 or EBV can be used with an appropriate selectable marker.

Bacterial and Yeast Expression Systems

In bacterial systems, a number of expression vectors can be selected depending upon the use intended for the PLC delta-1 polypeptide. For example, when a large quantity of a PLC delta-1 polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene), in which the sequence encoding the PLC delta-1 polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989 or pGEX vectors (Promega, Madison, Wis.) can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or Factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding PLC delta-1 polypeptides can be driven by any of a number of promoters. For example, viral promoters such as the 35S and 19S promoters of CaMV can be used alone or in combination with the omega leader sequence from TMV (Takamatsu *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl.*

Cell Differ. 17, 85–105, 1991). These constructs can be introduced into plant cells by direct DNA transformation or by pathogen-mediated transfection. Such techniques are described in a number of generally available reviews (see, for example, Hobbs or Murray, in MCGRAW HILL YEARBOOK OF SCIENCE AND TECHNOLOGY, McGraw Hill, New York, N.Y., pp. 191–

An insect system also can be used to express a PLC delta-1 polypeptide. For example, in one such system *Autographa californica* nuclear polyhedrosis virus (AcNPV) is used as a vector to express foreign genes in *Spodoptera frugiperda* cells or in Trichoplusia larvae. Sequences encoding PLC delta-1 polypeptides can be cloned into a non-essential region of the virus, such as the polyhedrin gene, and placed under control of the polyhedrin promoter. Successful insertion of PLC delta-1 polypeptides will render the polyhedrin gene inactive and produce recombinant virus lacking coat protein. The recombinant viruses can then be used to infect, for example, *S. frugiperda* cells or Trichoplusia larvae in which PLC delta-1 polypeptides can be expressed (Engelhard et al., Proc. Nat. Acad. Sci. 91, 3224–3227, 1994).

Mammalian Expression Systems

A number of viral-based expression systems can be utilized in mammalian host cells. For example, if an adenovirus is used as an expression vector, sequences encoding PLC delta-1 polypeptides can be ligated into an adenovirus transcription/translation complex consisting of the late promoter and tripartite leader sequence. Insertion in a non-essential E1 or E3 region of the viral genome can be used to obtain a viable virus which is capable of expressing a PLC delta-1 polypeptide in infected host cells (Logan & Shenk, Proc. Natl. Acad. Sci. 81, 3655–3659, 1984). In addition, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding PLC delta-1 polypeptides. Such signals include the ATG initiation codon and adjacent sequences. In cases where sequences encoding a PLC delta-1 polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., Results Probl. Cell Differ. 20, 125–162, 1994).

Host Cells

A host cell strain can be chosen for its ability to modulate the expression of the inserted sequences or to process an expressed PLC delta-1 polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110–2209) and can be chosen to ensure the correct modification and processing of the foreign protein.

Stable expression is preferred for long-term, high-yield production of recombinant proteins. For example, cell lines which stably express PLC delta-1 polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced PLC delta-1 sequences. Resistant clones of stably transformed cells can be proliferated using tissue culture techniques appropriate to the cell type.

Any number of selection systems can be used to recover transformed cell lines. These include, but are not limited to, the herpes simplex virus thymidine kinase (Wigler et al., Cell 11, 223–32, 1977) and adenine phosphoribosyltransferase (Lowy et al., Cell 22, 817–23, 1980). Genes which can be employed in $tk^-$ or $aprt^-$ cells, respectively. Also, antimetabolite, antibiotic, or herbicide resistance can be used as the basis for selection. For example, dhfr confers resistance to methotrexate (Wigler et al., Proc. Natl. Acad. Sci. 77, 3567–70, 1980); npt confers resistance to the amino-glycosides, neomycin and G-418 (Colbere-Garapin et al., J. Mol. Biol. 150, 1–14, 1981); and als and pat confer resistance to chlorsulfuron and phosphinotricin acetyltransferase, respectively (Murray, 1992 supra). Additional selectable genes have been described, for example trpB, which allows cells to utilize indole in place of tryptophan, or hisD, which allows cells to utilize histinol in place of histidine (Hartman & Mulligan, Proc. Natl. Acad. Sci. 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., Methods Mol. Biol. 55, 121–131, 1995).

Detecting Expression of Polypeptides

Although the presence of marker gene expression suggests that the PLC delta-1 polynucleotide is also present, its presence and expression may need to be confirmed. For example, if a sequence encoding a PLC delta-1 polypeptide is inserted within a marker gene sequence, transformed cells containing sequences which encode a PLC delta-1 polypeptide can be identified by the absence of marker gene function. Alternatively, a marker gene can be placed in tandem with a sequence encoding a PLC delta-1 polypeptide under the control of a single promoter. Expression of the marker gene in response to induction or selection usually indicates expression of the PLC delta-1 polynucleotide.

Alternatively, host cells which contain a PLC delta-1 polynucleotide and which express a PLC delta-1 polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein.

The presence of a polynucleotide sequence encoding a PLC delta-1 polypeptide can be detected by DNA-DNA or DNA-RNA hybridization or amplification using probes or fragments or fragments of polynucleotides encoding a PLC delta-1 polypeptide. Nucleic acid amplification-based assays involve the use of oligonucleotides selected from sequences encoding a PLC delta-1 polypeptide to detect transformants which contain a PLC delta-1 polynucleotide.

A variety of protocols for detecting and measuring the expression of a PLC delta-1 polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a PLC delta-1 polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding PLC delta-1 polypeptides include oligolabeling, nick translation, end-labeling, or PCR amplification using a labeled nucleotide. Alternatively, sequences encoding a PLC delta-1 polypeptide can be cloned into a vector for the production of an mRNA probe. Such vectors are known in the art, are commercially available, and can be used to synthesize RNA probes in vitro by addition of labeled nucleotides and an appropriate RNA polymerase, such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, fluorescent, chemiluminescent, or chromogenic agents, as well as substrates, cofactors, inhibitors, magnetic particles, and the like.

Expression and Purification of Polypeptides

Host cells transformed with nucleotide sequences encoding a PLC delta-1 polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode PLC delta-1 polypeptides can be designed to contain signal sequences which direct secretion of PLC delta-1 polypeptides through a prokaryotic or eukaryotic cell membrane.

Other constructions can be used to join a sequence encoding a PLC delta-1 polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen, San Diego, Calif.) between the purification domain and the PLC delta-1 polypeptide can be used to facilitate purification. One such expression vector provides for expression of a fusion protein containing a PLC delta-1 polypeptide and 6 histidine residues preceding a thioredoxin or an enterokinase cleavage site. The histidine residues facilitate purification on IMAC (immobilized metal ion affinity chromatography as described in Porath et al., *Prot. Exp. Purif.* 3, 263–281, 1992), while the enterokinase cleavage site provides a means for purifying the PLC delta-1 polypeptide from the fusion protein. Vectors which contain fusion proteins are disclosed in Kroll et al., *DNA Cell Biol.* 12, 441453, 1993).

Chemical Synthesis

Sequences encoding a PLC delta-1 polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a PLC delta-1 polypeptide itself can be produced using chemical methods to synthesize its amino acid sequence. For example, PLC delta-1 polypeptides can be produced by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Various fragments of PLC delta-1 polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, W H Freeman and Co., New York, N.Y., 1983). The composition of a synthetic PLC delta-1 polypeptide can be confirmed by amino acid analysis or sequencing (e.g., the Edman degradation procedure; see Creighton, supra). Additionally, any portion of the amino acid sequence of the PLC delta-1 polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce PLC delta-1 polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter PLC delta-1 polypeptide-encoding sequences for a variety of reasons, including modification of the cloning, processing, and/or expression of the gene product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a PLC delta-1 polypeptide. "Antibody" as used herein includes intact immunoglobulin molecules, as well as fragments thereof, such as Fab, F(ab')$_2$, and Fv, which are capable of binding an epitope of a PLC delta-1 polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a PLC delta-1 polypeptide can be used therapeutically, as well as in immunochemical assays, including but not limited to Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a PLC delta-1 polypeptide provides a detection signal at least 5-, 10-, or 20-fold higher than a detection signal provided with other proteins when used in an immunochemical assay. Preferably, antibodies which specifically bind to PLC delta-1 polypeptides do not detect other proteins in immunochemical assays and can immunoprecipitate a PLC delta-1 polypeptide from solution. PLC delta-1 polypeptides can be used to immunize a mammal, such as a mouse, rat, rabbit, guinea pig, monkey, or human, to produce polyclonal antibodies. If desired, a PLC delta-1 polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a PLC delta-1 polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, one can produce humanized antibodies using recombinant methods, as described in GB2188638B. Antibodies which specifically bind to a PLC delta-1 polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to PLC delta-1 polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61, 497–501; Nicholls et al., 1993, *J. Immunol. Meth.* 165, 81–91.

Antibodies which specifically bind to PLC delta-1 polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies of the invention can be purified by methods well known in the art. For example, antibodies can be affinity purified by passage over a column to which a PLC delta-1 polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of PLC delta-1 gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of PLC delta-1 gene expression can be obtained by designing antisense oligonucleotides which will form duplexes to the control, 5', or regulatory regions of the PLC delta-1 gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful duplex formation between an antisense oligonucleotide and the complementary sequence of a PLC delta-1 poly nucleotide. Antisense oligonucleotides which comprise, for example, 2, 3, 4, or 5 or more stretches of contiguous nucleotides which are precisely complementary to a PLC delta-1 polynucleotide, each separated by a stretch of contiguous nucleotides which are not complementary to adjacent PLC delta-1 nucleotides, can provide targeting specificity for PLC delta-1 mRNA Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular PLC delta-1 polynucleotide sequence.

Antisense oligonucleotides can be modified without affecting their ability to hybridize to a PLC delta-1 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a PLC delta-1 polynucleotide can be used to generate ribozymes which will specifically bind to mRNA transcribed from the PLC delta-1 polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a PLC delta-1 RNA target are initially identified by scanning the RNA molecule for ribozyme cleavage sites which include the following sequences: GUA, GUU, and GUC. Once identified, short RNA sequences of between 15 and 20 ribonucleotides corresponding to the region of the PLC delta-1 target RNA containing the cleavage site can be evaluated for secondary structural features which may render the target inoperable. The suitability of candidate targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related; thus, upon hybridizing to the PLC delta-1 target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease PLC delta-1 expression. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of PLC delta-1 mRNA occurs only when both a ribozyme and a target gene are induced in the cells.

Differentially Expressed Genes

Described herein are methods for the identification of genes whose products interact with human PLC delta-1. Such genes may represent genes that are differentially expressed in disorders including, but not limited to, COPD, congestive heart failure, hypertension, and cancer. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human PLC delta-1 gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., Proc. Natl. Acad. Sci. U.S.A. 85, 208–12, 1988), subtractive hybridization (Hedrick et al., Nature 308, 149–53; Lee et al., Proc. Natl. Acad. Sci. U.S.A. 88, 2825, 1984), and differential display (Liang & Pardee, Science 257, 967–71, 1992; U.S. Pat. No. 5,262,311), and microarrays.

The differential expression information may itself suggest relevant methods for the treatment of disorders involving the human PLC delta-1. For example, treatment may include a modulation of expression of the differentially expressed genes and/or the gene encoding the human PLC delta-1. The differential expression information may indicate whether the expression or activity of the differentially expressed gene or gene product or the human PLC delta-1 gene or gene product are up-regulated or down-regulated.

Screening Methods

The invention provides methods for identifying modulators, i.e., candidate or test compounds which bind to PLC delta-1 polypeptides or polynucleotides and/or have a stimulatory or inhibitory effect on, for example, expression or activity of the PLC delta-1 polypeptide or polynucleotide, so as to regulate degradation of the extracellular matrix. Decreased extracellular matrix degradation is useful for preventing or suppressing malignant cells from metastasizing. Increased extracellular matrix degradation may be desired, for example, in developmental disorders characterized by inappropriately low levels of extracellular matrix degradation or in regeneration.

The invention provides assays for screening test compounds which bind to or modulate the activity of a PLC delta-1 polypeptide or a PLC delta-1 polynucleotide. A test compound preferably binds to a PLC delta-1 polypeptide or polynucleotide. More preferably, a test compound decreases a PLC delta-1 activity of a PLC delta-1 polypeptide or expression of a PLC delta-1 polynucleotide by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412–421, 1992), or on beads (Lam, Nature 354, 82–84, 1991), chips (Fodor, Nature 364, 555–556, 1993), bacteria or spores (Ladner, U.S. Pat. No. 5,223,409), plasmids (Cull et al., Proc. Natl. Acad. Sci. U.S.A. 89, 1865–1869, 1992), or phage (Scott & Smith, Science 249, 386–390, 1990; Devlin, Science 249, 404–406, 1990); Cwirla et al., Proc. Natl. Acad. Sci. 97, 6378–6382, 1990; Felici, J. Mol. Biol. 222, 301–310, 1991; and Ladner, U.S. Pat. No. 5,223,409).

High Throughput Screening

Test compounds can be screened for the ability to bind to PLC delta-1 polypeptides or polynucleotides or to affect PLC delta-1 activity or PLC delta-1 gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., Proc. Natl. Acad. Sci.

U.S.A. 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Sahnon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies the active site or the fad-like domain of the PLC delta-1 polypeptide, thereby making the active site or fibronectin domain inaccessible to substrate such that normal biological activity is prevented. Examples of such small molecules include, but are not limited to, small peptides or peptide-like molecules. In binding assays, either the test compound or the PLC delta-1 polypeptide can comprise a detectable label, such as a fluorescent, radioisotopic, chemiluminescent, or enzymatic label, such as horseradish peroxidase, alkaline phosphatase, or luciferase. Detection of a test compound which is bound to the PLC delta-1 polypeptide can then be accomplished, for example, by direct counting of radioemmission, by scintillation counting, or by determining conversion of an appropriate substrate to a detectable product.

Alternatively, binding of a test compound to a PLC delta-1 polypeptide can be determined without labeling either of the interactants. For example, a microphysiometer can be used to detect binding of a test compound with a target polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a PLC delta-1 polypeptide. (McConnell et al., *Science* 257, 1906–1912, 1992).

Determining the ability of a test compound to bind to a PLC delta-1 polypeptide also can be accomplished using a technology such as real-time Bimolecular Interaction Analysis (BIA). Sjolander & Urbaniczky, *Anal. Chem.* 63, 2338–2345, 1991, and Szabo et al., *Curr. Opin. Struct. Biol.* 5, 699–705, 1995. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a PLC delta-1 polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the PLC delta-1 polypeptide and modulate its activity.

The two-hybrid system is based on the modular nature of most transcription factors, which consist of separable DNA-binding and activation domains. Briefly, the assay utilizes two different DNA constructs. For example, in one construct a polynucleotide encoding a PLC delta-1 polypeptide is fused to a polynucleotide encoding the DNA binding domain of a known transcription factor (e.g., GAL-4). In the other construct, a DNA sequence that encodes an unidentified protein ("prey" or "sample") is fused to a polynucleotide that codes for the activation domain of the known transcription factor. If the "bait" and the "prey" proteins are able to interact in vivo to form a protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the PLC delta-1 polypeptide.

It may be desirable to immobilize either the PLC delta-1 polypeptide (or polynucleotide) or the test compound to facilitate separation of bound from unbound forms of one or both of the interactants, as well as to accommodate automation of the assay. Thus, either the PLC delta-1 polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the PLC delta-1 polypeptide (or polynucleotide) or test compound to a solid support, including use of covalent and non-covalent linkages, passive absorption, or pairs of binding moieties attached respectively to the polypeptide or test compound and the solid support. Test compounds are preferably bound to the solid support in an array, so that the location of individual test compounds can be tracked. Binding of a test compound to a PLC delta-1 polypeptide (or polynucleotide) can be accomplished in any vessel suitable for containing the reactants. Examples of such vessels include microtiter plates, test tubes, and microcentrifuge tubes.

In one embodiment, a PLC delta-1 polypeptide is a fusion protein comprising a domain that allows the PLC delta-1 polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed PLC delta-1 polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing polypeptides or polynucleotides on a solid support also can be used in the screening assays of the invention. For example, either a PLC delta-1 polypeptide (or polynucleotide) or a test compound can be immobilized utilizing conjugation of biotin and streptavidin. Biotinylated PLC delta-1 polypeptides or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a PLC delta-1 polypeptide polynucleotides, or a test compound, but which do not interfere with a desired binding site, such as the active site or a fibronectin domain of the PLC delta-1 polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the PLC delta-1 polypeptide (or polynucleotides) or test compound, enzyme-linked assays which rely on detecting a PLC delta-1 activity of the PLC delta-1 polypeptide, and SDS gel electrophoresis under non-reducing conditions.

Screening for test compounds which bind to a PLC delta-1 polypeptide or polynucleotide also can be carried out in an intact cell. Any cell which comprises a PLC delta-1 polynucleotide or polypeptide can be used in a cell-based assay system.

A PLC delta-1 polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used. An intact cell is contacted with a test compound. Binding of the test compound to a PLC delta-1 polypeptide or polynucleotide is determined as described above, after lysing the cell to release the PLC delta-1 polypeptide-test compound complex.

Enzyme Assays

Test compounds can be tested for the ability to increase or decrease a PLC delta-1 activity of a PLC delta-1 polypeptide. PLC delta-1 activity can be measured as is known in the art, for example, using the method described in Grobler & Hurley, *Protein Sci.* 5, 680–86, 1996. PLC delta-1 activity can be measured after contacting either a purified PLC delta-1 polypeptide, a cell extract, or an intact cell with a test compound. A test compound which decreases PLC delta-1 activity by at least about 10, preferably about 50, more preferably about 75, 90, or 100% is identified as a potential therapeutic agent for decreasing human PLC delta-1 activity. A test compound which increases PLC delta-1 activity by at least about 10, preferably about 50, more preferably about 75, 90, or 100% is identified as a potential therapeutic agent for increasing human PLC delta-1 activity.

Gene Expression

In another embodiment, test compounds which increase or decrease PLC delta-1 gene expression are identified. A PLC delta-1 polynucleotide is contacted with a test compound, and the expression of an RNA or polypeptide product of the PLC delta-1 polynucleotide is determined. The level of expression of PLC delta-1 mRNA or polypeptide in the presence of the test compound is compared to the level of expression of PLC delta-1 mRNA or polypeptide in the absence of the test compound. The test compound can then be identified as a modulator of expression based on this comparison. For example, when expression of PLC delta-1 mRNA or polypeptide is greater in the presence of the test compound than in its absence, the test compound is identified as a stimulator or enhancer of PLC delta-1 mRNA or polypeptide is less expression. Alternatively, when expression of the mRNA or protein is less in the presence of the test compound than in its absence, the test compound is identified as an inhibitor of PLC delta-1 mRNA or polypeptide expression.

The level of PLC delta-1 mRNA or polypeptide expression in the cells can be determined by methods well known in the art for detecting mRNA or protein. Either qualitative or quantitative methods can be used. The presence of polypeptide products of a PLC delta-1 polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a PLC delta-1 polypeptide.

Such screening can be carried out either in a cell-free assay system or in an intact cell. Any cell which expresses a PLC delta-1 polynucleotide can be used in a cell-based assay system. The PLC delta-1 polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used.

Pharmaceutical Compositions

The invention also provides pharmaceutical compositions which can be administered to a patient to achieve a therapeutic effect. Pharmaceutical compositions of the invention can comprise a PLC delta-1 polypeptide, PLC delta-1 polynucleotide, antibodies which specifically bind to a PLC delta-1 polypeptide, or mimetics, agonists, antagonists, or inhibitors of a PLC delta-1 polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxy-propy-lmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Diagnostic Methods

The human PLC delta-1 and polynucleotides encoding it can be used in diagnostic assays for detecting diseases and abnormalities or susceptibility to diseases and abnormalities related to the presence of mutations in the nucleic acid sequences which encode the enzyme. For example, differences can be determined between the cDNA or genomic sequence encoding human PLC delta-1 in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of human PLC delta-1 also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

Therapeutic Indications and Methods

Diseases or conditions in which signal transduction is aberrant may be treated using molecules which regulate the activity of human PLC delta-1.

Human PLC delta-1 can be regulated to treat COPD, congestive heart failure, hypertension, and cancer. Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders*, 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Congestive heart failure results in alterations of the level of PLC isozymes, including PLC delta-1 (Tappia et al., *Am. J. Physiol.* 227, H40-9, 1999); correction of PLC delta-1 levels may therefore be useful to treat congestive heart failure. Heart failure is defined as a pathophysiologic state in which an abnormality of cardiac function is responsible for the failure of the heart to pump blood at a rate commensurate with the requirement of the metabolizing tissue. It includes all forms of pumping failure such as high-output and low-output, acute and chronic, right-sided or left-sided, systolic or diastolic, independent of the underlying cause.

Studies on spontaneous hypertensive rats have suggested that one of the main causes for the hypertension is an abnormal activation of PLC delta-1 resulting from point mutations in the X and Y regions of the PLC amino acid sequence. Thus, regulation of human PLC delta-1 can be used to treat hypertension. Hypertensive vascular diseases include primary as well as all kinds of secondary arterial hypertension (renal, endocrine, neurogenic, others). Human PLC delta-1 may therefore be used as a drug target for the treatment of hypertension as well as for the prevention of all complications.

Human PLC delta-1 also may be useful for treating cancer. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

The invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects PLC delta-1 activity can be administered to a human cell, either in vitro or in vivo, to reduce PLC delta-1 activity. The reagent preferably binds to an expression product of a human PLC delta-1 gene. If the expression product is a polypeptide, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung or liver.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmol of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a tumor cell, such as a tumor cell ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol:* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Determination of a Therapeutically Effective Dose

The determination of a therapeutically effective dose is well within the capability of those skilled in the art. A therapeutically effective dose refers to that amount of active ingredient which increases or decreases extracellular matrix degradation relative to that which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of a PLC delta-1 polynucleotide or activity of a PLC delta-1 polypeptide by at least about 10, preferably about 50, more preferably about 75, 90, or 100% relative to the absence of the reagent. The effectiveness of the mechanism chosen to decrease the level of expression of a PLC delta-1 polynucleotide or the activity of a PLC delta-1 polypeptide can be assessed using methods well known in the art, such as hybridization of nucleotide probes to PLC delta-1-specific mRNA, quantitative RT-PCR, immunologic detection of a PLC delta-1 polypeptide, or measurement of PLC delta-1 activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

The above disclosure generally describes the present invention, and all patents, patent applications, and references cited in this disclosure are expressly incorporated herein by references in their entireties. A more complete understanding can be obtained by reference to the following specific examples, which are provided for purposes of illustration only and are not intended to limit the scope of the invention.

EXAMPLE 1

Detection of PLC Delta-1 Activity

The polynucleotide of SEQ ID NO: 10 is inserted into the expression vector pCEV4 and the expression vector pCEV4-PLC delta 1 polypeptide obtained is transfected into human embryonic kidney 293 cells. Cells at 80–90% confluence, in 24-well multiwells, are labeled overnight with myo-[2–3H] inositol (1 µCi mll, 0,5 ml/well) in medium M199 with 25 IU ml-l penicillin, 25 µg ml-l streptomycin, at 37° C. in 5% $CO_2$. To the 0,5 ml of labeling medium is added 50 µl of 11-fold final concentration of LiCl (110 mM) in balanced salt solution. After further incubation for 15 min with agonists, total [3H] inositol (poly)phosphates are extracted and separated on small Dowex-1 (Cl–) columns. It is shown that the polypeptide of SEQ ID NO.: 13 has PLC delta-1 activity.

EXAMPLE 2

Expression of a Recombinant DNA Sequence Encoding a Human PLC Delta-1 Polypeptide in Yeast Cells (*Pichia pastoris*)

To produce large quantities of human PLC delta-1 polypeptides in yeast, the *Pichia pastoris* expression vector pPICZB (Invitrogen, San Diego, Calif.) is used. The human PLC delta-1 encoding DNA sequence is the nucleotide sequence shown in SEQ ID NO:10. Before insertion into vector pPICZB, the DNA sequence is modified by well known methods in such a way that it contains at its 5'-end an initiation codon and at its 3'-end an enterokinase cleavage site, a His6 reporter tag, and a termination codon. Recognition sequences for restriction endonucleases are added at both termini. After digestion of the multiple cloning site of pPICZB with the corresponding restriction enzymes, the modified human PLC delta-1 polypeptide-encoding DNA sequence is ligated into pPICZB. This expression vector is designed for inducible expression in *Pichia pastoris*, and expression is driven by a yeast promoter. The resulting pPICZ/md-His6 vector is used to transform the yeast. The yeast is cultivated under usual conditions in shake flasks, and the recombinantly produced protein is isolated from the culture by affinity chromatography (Ni-NTA-Resin) in the presence of 8 M urea. The bound polypeptide is eluted with buffer, pH 3.5, and neutralized. Separation of the human PLC delta-1 polypeptide from the His6 reporter tag is accomplished by site-specific proteolysis using enterokinase (Invitrogen, San Diego, Calif.) according to manufacturer s instructions. Purified human PLC delta-1 polypeptide is obtained.

EXAMPLE 3

Identification of a Test Compound which Binds to a PLC Delta-1 Polypeptide

Purified PLC delta-1 polypeptides comprising a glutatlione-S-transferase protein and absorbed onto glutathione-derivatized wells of 96-well microtiter plates are contacted with test compounds from a small molecule library at pH 7.0 in a physiological buffer solution. PLC delta-1 polypeptides consist essentially of the amino acid sequence shown in SEQ ID NO:13. The test compounds comprise a fluorescent tag. The samples are incubated for 5 minutes to one hour. Control samples are incubated in the absence of a test compound.

The buffer solution containing the test compounds is washed from the wells. Binding of a test compound to a PLC delta-1 polypeptide is detected by fluorescence measurements of the contents of the wells. A test compound which increases the fluorescence in a well by at least 15% relative to fluorescence of a well in which a test compound was not incubated is identified as a compound which binds to a PLC delta-1 polypeptide.

EXAMPLE 4

Identification of a Test Compound which Decreases PLC Delta-1 Activity

Cellular extracts from cells comprising human PLC delta-1 are contacted with test compounds from a small molecule library and assayed for PLC delta-1 activity. Control extracts, in the absence of a test compound, also are assayed. Phospholipase activity can be measured, for example, as described in Grobler & Hurley, *Protein Sci.* 5, 680–86, 1996.

A test compound which decreases PLC delta-1 activity of the extract relative to the control extract by at least 20% is identified as a PLC delta-1 inhibitor.

EXAMPLE 5

Identification of a Test Compound which Decreases PLC Delta-1 Gene Expression

A test compound is administered to a culture of the breast tumor cell line MDA-468 and incubated at 37° C. for 10 to 45 minutes. A culture of the same type of cells incubated for the same time without the test compound provides a negative control.

RNA is isolated from the two cultures as described in Chirgwin et al., *Biochem.* 18, 5294–99, 1979). Northern blots are prepared using 20 to 30 µg total RNA and hybridized with a $^{32}P$-labeled PLC delta-l-specific probe at 65° C.

in Express-hyb (CLONTECH). The probe comprises at least 11 contiguous nucleotides selected from the complement of SEQ ID NO:10. A test compound which decreases the PLC delta-1-specific signal relative to the signal obtained in the absence of the test compound is identified as an inhibitor of PLC delta-1 gene expression.

EXAMPLE 6

Treatment of Hypertension with a Reagent which Specifically Binds to a Human PLC Delta-1 Gene Product Synthesis of antisense human PLC delta-1 oligonucleotides comprising at least 11 contiguous nucleotides selected from the complement of SEQ ID NO:10 is performed on a Pharmacia Gene Assembler series synthesizer using the phosphoramidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the *Limulus* Amebocyte Assay (Bang, *Biol. Bull.* (Woods Hole, Mass.) 105, 361–362, 1953).

An aqueous composition containing the antisense oligonucleotides at a concentration of 0.1–100 μM is administered to a patient with hypertension. The severity of the patient's hypertension is decreased.

EXAMPLE 7

In Vivo Testing of Compounds/Target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value≦0.05 compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at p≦0.05 as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value≦0.05 compared to the vehicle control group.

2.2. Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at p≦0.05 as compared to the vehicle control group.

2.3. Anti-angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is p≦0.05 as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at p≦0.05 as compared to the vehicle control group.

3. Primary Antitumor Efficacy 3.1. Early Therapy Models 3.1.1. Subcutaneous Tumor Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Antitumor efficacy may be initially determined by comparing the size of treated (T) and control (C) tumors on a given day by a Student's t-test, after the variance between groups is compared by an F-test, with significance determined at p≦0.05. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p≦0.05.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is p≦0.05 by a log-rank test compared to the control group in the experiment.

3.2. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is p≦0.05 as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value ≦0.05 compared to the vehicle control group.

3.3. Orthotopic Disease Models 3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is p≦0.05 as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value≦0.05 compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at p≦0.05 compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions throught e abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is p≦0.05 as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at p≦0.05 compared to the control group in the experiment.

3.3.3. Intrabronchial Assay

Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is p≦0.05 as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at p≦0.05 compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is p≦0.05 as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at p≦0.05 compared to the control group in the experiment.

4. Secondary (Metastatic) Antitumor Efficacy 4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is p≦0.05 by a log-rank test compared to the control group in the experiment. The mean number of visible tumor foci, as determined under a dissecting microscope, and the mean target organ weights are compared by Student's t-test after conducting an F-test, with significance determined at p≦0.05 compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is p≦0.05 by a log-rank test compared to the control group in the experiment. The mean number of visible tumor foci, as determined under a dissecting microscope, and the mean target organ weights are compared by Student's t-test after conducting an F-test, with significance at p≦0.05 compared to the vehicle control group in the experiment for both endpoints.

EXAMPLE 8

Tissue-Specific Expression of Human PLC Delta-1

As a first step to establishing a role for human PLC delta-1 in the pathogenesis of COPD, expression profiling of the gene was done using real-time quantitative PCR (TaqMan) with RNA samples isolated from a wide range of human cells and tissues. Total RNA samples were either purchased from commercial suppliers or purified in-house. Two panels of RNAs were used for profiling: a whole body organ panel (Table 1) and a respiratory specific panel (Table 2).

Real-time quantitative PCR. This technique is a development of the kinetic analysis of PCR first described by Higuchi et al. (*BioTechnology* 10, 413–17, 1992; *BioTechnology* 11, 1026–30, 1993). The principle is that at any given cycle within the exponential phase of PCR, the amount of product is proportional to the initial number of template copies. PCR amplification is performed in the presence of an oligonucleotide probe (TaqMan probe) that is complementary to the target sequence and labeled with a fluorescent reporter dye and a quencher dye. During the extension phase of PCR, the probe is cleaved by the 5'-3' endonuclease activity of Taq DNA polymerase, releasing the fluorophore from the effect of the quenching dye (Holland et al., *Proc. Natl. Acad. Sci. U.S.A.* 88, 7276–80, 1991). Because the fluorescence emission increases in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

RNA extraction and cDNA preparation. Total RNA from each of the 'in-house' samples listed in Table 2 was isolated using Qiagen's (Crawley, West Sussex, UK) RNeasy system according to the manufacturer's protocol. The concentration of purified RNA was determined using RiboGreen RNA quantitation kit (Molecular Probes Europe, The Netherlands). RNA concentrations of the samples purchased from commercial suppliers were also determined using RiboGreen. For the preparation of cDNA, 1 μg of total RNA was reverse transcribed using 200U of SUPERSCRIPT™ II RNaseH⁻ Reverse Transcriptase (Life Technologies, Paisley, UK), 10 mM dithiothreitol, 0.5 mM of each dNTP, and 5 μM random hexamers (PE Applied Biosystems, Warrington, Cheshire, UK) in a final volume of 20 μl according to the manufacturer's protocol.

TaqMan quantitative analysis. Specific primers and probe were designed according to the recommendations of PE Applied Biosystems and are listed below:

```
Forward primer:
5'-CTGAGCGTGTGGTTCCAGC-3'

Reverse primer:
5'-CAGGCCCTCGGACTGGT-3'
```

-continued

```
Probe:
5'-(FAM)-ACATCTTCTTCGTGCAGCACATCGAGG-3'
where FAM = 6-carboxy-fluorescein.
```

Quantitative PCR was performed with 10 ng of reverse transcribed RNA from each sample. Each determination was done in duplicate.

The assay reaction mix was as follows: 1× final TaqMan Universal PCR Master Mix (from 2× stock) (PE Applied Biosystems, CA); 900 nM forward primer; 900 nM reverse primer; 200 nM probe; 10 ng cDNA; and water to 25 μl.

Each of the following steps were carried out once: pre PCR, 2 minutes at 50° C., and 10 minutes at 95° C. The following steps are carried out 40 times: denaturation, 15 seconds at 95° C., annealing/extension, 1 minute at 60° C.

Real-time quantitative PCR was done using an ABI Prism 7700 Sequence Detector. The $C_T$ value generated for each reaction was used to determine the initial template concentration (copy number) by interpolation from a universal standard curve. The level of expression of the target gene in each sample was calculated relative to the sample with the lowest expression of the gene.

The relative expression of human PLC delta-1 across various human tissues is shown in FIG. 16. Expression of the gene was detected in many tissues and was especially high in colon and testis. Abundant expression of human PLC delta-1 in lung was observed—although much lower than in colon and testis—and is of particular interest. This was investigated further by analyzing the expression of the gene in some of the constituent cell types of the lung. In these samples expression was essentially limited to epithelial cells, with small airway epithelial cells and the Clara-like cell line H441 exhibiting the highest levels (FIG. 17). Expression in inflammatory cells was absent or very low.

TABLE 1

Human organ RNA panel used for real-time quantitative PCR.
All samples were obtained from Clontech UK Ltd, Basingstoke, UK.

| Tissue | Cat. # |
| --- | --- |
| Adrenal gland | Human Panel V, K4004-1 |
| Bone marrow | Human Panel II, K4001-1 |
| Brain | Human Panel I, K4000-1 |
| Colon | Human Panel II, K4001-1 |
| Heart | Human Panel III, K4002-1 |
| Kidney | Human Panel I, K4000-1 |
| Liver | Human Panel I, K4000-1 |
| Lung | Human Panel I, K4000-1 |
| Mammary gland | Human Panel III, K4002-1 |
| Pancreas | Human Panel V, K4004-1 |
| Prostate | Human Panel III, K4002-1 |
| Salivary gland | Human Panel V, K4004-1 |
| Skeletal muscle | Human Panel III, K4002-1 |
| Small intestine | Human Panel II, K4001-1 |
| Spleen | Human Panel II, K4001-1 |
| Stomach | Human Panel II, K4001-1 |
| Testis | Human Panel III, K4002-1 |
| Thymus | Human Panel II, K4001-1 |
| Thyroid | Human Panel V, K4004-1 |
| Uterus | Human Panel III, K4002-1 |

TABLE 2

Human respiratory specific RNA panel used for real-time quantitative PCR.

| Tissue/cell type | Supplier, cat # |
| --- | --- |
| Lung (fetal) | Takara (Japan) |
| Lung | Clontech, Human Panel I, K4000-1 |
| Trachea | Clontech, Human Panel I, K4000-1 |
| Cultured human bronchial epithelial cells | In-house |
| Cultured airway smooth muscle cells | In-house |
| Cultured small airway epithelial cells | In-house |
| Primary cultured alveolar type II cells | In-house |
| Cultured H441 cells (Clara-like) | In-house |
| Freshly isolated polymorphonuclear leukocytes (neutrophils) | In-house |
| Freshly isolated monocytes | In-house |
| Cultured monocytes (macrophage-like) | In-house |

The invention claimed is:

1. A method of screening for candidate binding agents, comprising the steps of:

contacting a protein comprising the amino acid sequence shown in SEQ ID NO:13 with a test compound;

assaying for binding between the protein and the test compound; and identifying a test compound that binds to the protein as a candidate binding agent that may be useful for regulating activity of the protein.

2. The method of claim 1 wherein either the test compound or the protein comprises a detectable label.

3. The method of claim 1 wherein either the test compound or the protein is bound to a solid support.

* * * * *

SEQUENCE LISTING

```
<160> NUMBER OF SEQ ID NOS: 13

<210> SEQ ID NO 1
<211> LENGTH: 420
<212> TYPE: DNA
<213> ORGANISM: Homo sapiens

<400> SEQUENCE: 1
cggccgctgg aggcgttgcc gccgcccgcc cgaggagccc ccggtggccg cccaggtcgc    60
      agcccaagtc gcggcgccgg tcgctctccc gtccccgccg actccctccg atggcggcac   120
      caagaggccc gggctgcggg cgctgaagaa gatgggcctg acggaggacg aggacgtgcg   180
      cgccatgctg cggggctccc ggctccgcaa gatccgctcg cgcacgtggc acaaggagcg   240
      gctgtaccgg ctgcaggagg acggcctgag cgtgtggttc cagcggcgca tcccgcgtgc   300
      gccatcgcag cacatcttct tcgtgcagca catcgaggcg gtccgcgagg gccaccagtc   360
```

```
cgagggcctg cggcgcttcg ggggtgcctt cgcgccagcg cgctgcctca ccatcgcctt    420
```

<210> SEQ ID NO 2
<211> LENGTH: 139
<212> TYPE: PRT
<213> ORGANISM: Homo sapiens

<400> SEQUENCE: 2

```
Gly Arg Trp Arg Arg Cys Arg Arg Pro Pro Glu Glu Pro Pro Val Ala
  1               5                  10                  15
Ala Gln Val Ala Ala Gln Val Ala Ala Pro Val Ala Leu Pro Ser Pro
             20                  25                  30
Pro Thr Pro Ser Asp Gly Gly Thr Lys Arg Pro Gly Leu Arg Ala Leu
         35                  40                  45
Lys Lys Met Gly Leu Thr Glu Asp Glu Asp Val Arg Ala Met Leu Arg
     50                  55                  60
Gly Ser Arg Leu Arg Lys Ile Arg Ser Arg Thr Trp His Lys Glu Arg
 65                  70                  75                  80
Leu Tyr Arg Leu Gln Glu Asp Gly Leu Ser Val Trp Phe Gln Arg Arg
                 85                  90                  95
Ile Pro Arg Ala Pro Ser Gln His Ile Phe Phe Val Gln His Ile Glu
            100                 105                 110
Ala Val Arg Glu Gly His Gln Ser Glu Gly Leu Arg Arg Phe Gly Gly
        115                 120                 125
Ala Phe Ala Pro Ala Arg Cys Leu Thr Ile Ala
    130                 135
```

<210> SEQ ID NO 3
<211> LENGTH: 504
<212> TYPE: DNA
<213> ORGANISM: Homo sapiens

<400> SEQUENCE: 3

```
gcggccgctg gaggcgttgc cgccgcccgc ccgaggagcc cccggtggcc gcccaggtcg     60
cagcccaagt cgcggcgccg gtcgctctcc cgtccccgcc gactccctcc gatggcggca    120
ccaagaggcc cgggctgcgg gcgctgaaga gatgggcct gacgggagac gaggacgtgc    180
gcgccatgct gcggggctcc cggctccgca agatccgctc gcgcacgtgg cacaaggagc    240
ggctgtaccg gctgcaggag gacggcctga gcgtgtggtt ccagcggcgc atcccgcgtg    300
cgccatcgca gcacatcttc ttcgtgcagc acatcgaggc ggtccgcgag ggccaccagt    360
ccgagggcct gcggcgcttc ggggtgcct tcgcgccagc gcgctgcctc accatcgcct    420
tcaagggccg ccgcaagaac ctggacctgg cggcgcccac ggctgaggaa gcgcagcgct    480
gggtgcgcgg tctgaccaag ctcc                                          504
```

<210> SEQ ID NO 4
<211> LENGTH: 167
<212> TYPE: PRT
<213> ORGANISM: Homo sapiens

<400> SEQUENCE: 4

```
Gly Arg Trp Arg Arg Cys Arg Arg Pro Pro Glu Glu Pro Pro Val Ala
  1               5                  10                  15
Ala Gln Val Ala Ala Gln Val Ala Ala Pro Val Ala Leu Pro Ser Pro
             20                  25                  30
Pro Thr Pro Ser Asp Gly Gly Thr Lys Arg Pro Gly Leu Arg Ala Leu
         35                  40                  45
Lys Lys Met Gly Leu Thr Glu Asp Glu Asp Val Arg Ala Met Leu Arg
     50                  55                  60
Gly Ser Arg Leu Arg Lys Ile Arg Ser Arg Thr Trp His Lys Glu Arg
 65                  70                  75                  80
Leu Tyr Arg Leu Gln Glu Asp Gly Leu Ser Val Trp Phe Gln Arg Arg
                 85                  90                  95
Ile Pro Arg Ala Pro Ser Gln His Ile Phe Phe Val Gln His Ile Glu
            100                 105                 110
Ala Val Arg Glu Gly His Gln Ser Glu Gly Leu Arg Arg Phe Gly Gly
        115                 120                 125
Ala Phe Ala Pro Ala Arg Cys Leu Thr Ile Ala Phe Lys Gly Arg Arg
    130                 135                 140
Lys Asn Leu Asp Leu Ala Ala Pro Thr Ala Glu Glu Ala Gln Arg Trp
145                 150                 155                 160
Val Arg Gly Leu Thr Lys Leu
                165
```

<210> SEQ ID NO 5
<211> LENGTH: 490
<212> TYPE: DNA
<213> ORGANISM: Homo sapiens

<400> SEQUENCE: 5

```
gcggccgctg gaggcgttgc cgccgcccgc ccgaggagcc cccggtggcc gcccaggtcg    60
cagcccaagt cgcggcgccg gtcgctctcc cgtccccgcc gactccctcc gatggcggca   120
ccaagaggcc cgggctgcgg gcgctgaaga agatgggcct gacggaggac gaggacgtgc   180
gcgccatgct gcggggctcc cggctccgca agatccgctc gcgcacgtgg cacaaggagc   240
ggctgtaccg gctgcaagag gacgggctga gcgtgtggtt cagcggcgca tcccgcgtgc   300
gccatcgcag cacatcttct tcgtgcagca catcgaggcg gtccgcgagg gccaccagtc   360
cgagggcctg cggcgcttcg ggggtgcctt cgcgccagcg cgctgcctca ccatcgcctt   420
caagggccgc cgcaagaacc tggacctggc ggcgcccacg gctgaggaag cgcagcgctg   480
ggtgcgcggt                                                          490
```

<210> SEQ ID NO 6
<211> LENGTH: 469
<212> TYPE: DNA
<213> ORGANISM: Homo sapiens

<400> SEQUENCE: 6

```
gcggccgctg gaggcgttgc cgccgcccgc ccgaggagcc cccggtggcc gcccaggtcg    60
cagcccaagt cgcggcgccg gtcgctctcc cgtccccgcc gactccctcc gatggcggca   120
ccaagaggcc cgggctgcgg gcgctgaaga agatgggcct gacggaggac gaggacgtgc   180
gcgccatgct gcggggctcc cggctccgca agatccgctc gcgcacgtgg cacaaggagc   240
ggctgtaccg gctgcaggag gacggcctga gcgtgtggtt ccagcggcgc atcccgcgtg   300
cgccatcgca gcacatcttc ttcgtgcagc acatcgaggc ggtccgcgag ggccaccagt   360
ccgagggcct gcggcgcttc ggggtgcct tcgcgccagc gcgctgcctc accatcgcct   420
tcaagggccg ccgcaagaac ctggacctgg cggcgcccac ggctgagga              469
```

<210> SEQ ID NO 7
<211> LENGTH: 379
<212> TYPE: DNA
<213> ORGANISM: Homo sapiens

<400> SEQUENCE: 7

```
gcggccgctg gaggcgttgc cgccgcccgc ccgaggagcc cccagtggcc gcccaggtcg    60
cagcccaagt cgcggcgccg gtcgctctcc cgtccccgcc gactccctcc gatggcggca   120
ccaagaggcc cgggctgcgg gcgctgaaga agatgggcct gacggaggac gaggacgtgc   180
gcgccatgct gcggggctcc cggctccgca agatccgctc gcgcacgtgg cacaaggagc   240
ggctgtaccg gctgcaggag gacggcctga gcgtgtggtt ccagcggcgc atgccgcgtg   300
cgccatcgca gcacatcttc ttcgtgcagc acatcgaggc ggtccgcgag ggccaccagt   360
ccgagggcct gcggcgctt                                                379
```

<210> SEQ ID NO 8
<211> LENGTH: 292
<212> TYPE: DNA
<213> ORGANISM: Homo sapiens

<400> SEQUENCE: 8

```
gcggccgctg gaggcgttgc cgccgcccgc ccgaggagcc cccagtggccg cccaggtcgc    60
agcccaagtc gcggcgccgg tcgctctccc gtccccgccg actccctccg atggcggcac   120
caagaggccc gggctgcggg cgtgaagaa gatgggcctg acggaggacg aggacgtgcg   180
cgccatgctg cggggctccc ggctccgcaa gatccgctcg cgcacgtggg acaaggagcg   240
gctgtaccgg ctgcaggagg acggcctgag cgtgtggttc agcggcgca tc            292
```

<210> SEQ ID NO 9
<211> LENGTH: 43
<212> TYPE: PRT
<213> ORGANISM: Homo sapiens

<400> SEQUENCE: 9

```
    Trp Ile His Ser Tyr Leu His Arg Ala Asp Ser Asn Gln Asp Ser Lys
    1               5                   10                  15
    Met Ser Phe Lys Glu Ile Lys Ser Leu Leu Arg Met Val Asn Val Asp
                20                  25                  30
    Met Asn Asp Met Tyr Ala Tyr Leu Leu Phe Lys
                35                  40
```

<210> SEQ ID NO 10
<211> LENGTH: 2238
<212> TYPE: DNA
<213> ORGANISM: Homo sapiens

<400> SEQUENCE: 10

```
atgggcctga cggaggacga ggacgtgcgc gccatgctgc ggggctcccg gctccgcaag   60
atccgctcgc gcacgtggca caaggagcgg ctgtaccggc tgcaggagga cggcctgagc  120
gtgtggttcc agcggcgcat cccgcgtgcg ccatcgcagc acatcttctt cgtgcagcac  180
atcgaggcgg tccgcgaggg ccaccagtcc gagggcctgc ggcgcttcgg gggtgccttc  240
gcgccagcgc gctgcctcac catcgccttc aagggccgcc gcaagaacct ggacctggcg  300
gcgcccacgg ctgaggaagc gcagcgctgg gtgcgcggtg ggggtgactt accagccagt  360
tacctgaggg ctgggggcag cctggcgtgt tgctgttatt tcctgagcac ccacacctgg  420
atccactcct atctgcaccg ggctgactcc aaccaggaca gcaagatgag cttcaaggag  480
atcaagagcc tgctgagaat ggtcaacgtg gacatgaacg acatgtacgc ctacctcctc  540
ttcaaggagt gtgaccactc caacaacgac cgtctagagg gggctgagat cgaggagttc  600
ctgcggcgg ctgctgaagcg gccggagctg gaggagatct tccatcagta ctcgggcgag  660
accgcgtgc tgagtgcccc tgagctgctg gagttcctgg aggaccaggg cgaggagggc  720
gccacactgg cccgcgccca gcagctcatt cagacctatg agctcaacga gacagccaag  780
cagcatgagc tgatgacact ggatggcttc atgatgtacc tgttgtcgcc ggagggggct  840
gccttggaca cacccacac gtgtgtgttc caggacatga accagccccct gcccactac   900
ttcatctctt cctcccacaa caccatctg actgactccc agatcggggg gcccagcagc  960
accgaggcct atgttaggcg ctttgcccag ggatgccgct gcgtggagct ggactgctgg 1020
gaggggccag gaggggagcc cgtcatctat catggccata ccctcacctc caagattctc 1080
ttccgggacg tggtccaagc cgtgcgcgac catgccttca cgctgtcccc ttaccctgtc 1140
atcctatccc tggagaacca ctgcgggctg gagcagcagg ctgccatggc ccgccacctc 1200
tgcaccatcc tgggggacat gctggtgaca caggcgtgga tcccgaggag 1260
ctgccatccc cagagcagct gaagggccgg gtcctggtga agggaaagaa gttgcccgct 1320
gctcggagcg aggatggccg ggctctgtcg gatcgggagg aggaggagga ggatgacgag 1380
gaggaagaag aggaggtgga ggctgcagcg cagaggcggc tggtgagagc tgggatggat 1440
ctccccggag ctgtccggcc tggctgtgta ctgccacgc acccgcctgc gacctgcac 1500
cctgcccca acgcccaca accctgccag gtcagctccc cagcgagcg caaagccaag 1560
aaactcattc gggaggcagg aacagctttt gtcaggcaca tgcccgcca gctgacccgc 1620
gtgtacccgc tggggctgcg gatgaactca gccaactaca gtccccagga gatgtggaac 1680
tcgggcctgt cagctggtgg ccttgaacttc cagacgccag gctacgagat ggacctcaat 1740
gccgggcgct tcctagtcaa tgggcagtgt ggctacgtcc taaaacctgc ctgcctgcgg 1800
caacctgact cgacctttga ccccgagtac ccaggacctc ccagaaccac tctcagcatc 1860
caggtgctga ctgcacagca gctgcccaag ctgaatgccg agaagccaca ctccattgtg 1920
gaccccctgg tgcgcattga gatcatgggg gtgcccgcag actgtgcccg gcaggagact 1980
gactacgtgc tcaacaatgg cttcaaccccc cgctggggc agacctgca gttccagctg 2040
cgggctccgg agctggcact ggtccggttt gtggtggaag attatgacgc cacctcccc 2100
aatgactttg tgggccagtt tacactgcct cttagcagcc taaagcaagg gtaccgccac 2160
atacacctgc tttccaagga cggggcctca ctgtcaccag ccacgctctt catccaaatc 2220
cgcatccagc gctcctga                                                2238
```

<210> SEQ ID NO 11
<211> LENGTH: 756
<212> TYPE: PRT
<213> ORGANISM: Rattus norvegicus

<400> SEQUENCE: 11

```
Met Asp Ser Gly Arg Asp Phe Leu Thr Leu His Gly Leu Gln Asp Asp
  1               5                  10                  15
Pro Asp Leu Gln Ala Leu Leu Lys Gly Ser Gln Leu Leu Lys Val Lys
                 20                  25                  30
Ser Ser Ser Trp Arg Arg Glu Arg Phe Tyr Lys Leu Gln Glu Asp Cys
             35                  40                  45
Lys Thr Ile Trp Gln Glu Ser Arg Lys Val Met Arg Ser Pro Glu Ser
         50                  55                  60
Gln Leu Phe Ser Ile Glu Asp Ile Gln Glu Val Arg Met Gly His Arg
     65                  70                  75                  80
Thr Glu Gly Leu Glu Lys Phe Ala Arg Asp Ile Pro Glu Asp Arg Cys
                 85                  90                  95
Phe Ser Ile Val Phe Lys Asp Gln Arg Asn Thr Leu Asp Leu Ile Ala
                100                 105                 110
Pro Ser Pro Ala Asp Ala Gln His Trp Val Gln Gly Leu Arg Lys Ile
            115                 120                 125
Ile His His Ser Gly Ser Met Asp Gln Arg Gln Lys Leu Gln His Trp
        130                 135                 140
Ile His Ser Cys Leu Arg Lys Ala Asp Lys Asn Lys Asp Asn Lys Met
    145                 150                 155                 160
Asn Phe Lys Glu Leu Lys Asp Phe Leu Lys Glu Leu Asn Ile Gln Val
                165                 170                 175
Asp Asp Gly Tyr Ala Arg Lys Ile Phe Arg Glu Cys Asp His Ser Gln
                180                 185                 190
```

-continued

```
Thr Asp Ser Leu Glu Asp Glu Ile Glu Thr Phe Tyr Lys Met Leu
        195                 200                 205
Thr Gln Arg Ala Glu Ile Asp Arg Ala Phe Glu Glu Ala Ala Gly Ser
210                 215                 220
Ala Glu Thr Leu Ser Val Glu Arg Leu Val Thr Phe Leu Gln His Gln
225                 230                 235                 240
Gln Arg Glu Glu Ala Gly Pro Ala Leu Ala Leu Ser Leu Ile Glu
                245                 250                 255
Arg Tyr Glu Pro Ser Glu Thr Ala Lys Ala Gln Arg Gln Met Thr Lys
        260                 265                 270
Asp Gly Phe Leu Met Tyr Leu Leu Ser Ala Asp Gly Asn Ala Phe Ser
        275                 280                 285
Leu Ala His Arg Arg Val Tyr Gln Asp Met Asp Gln Pro Leu Ser His
        290                 295                 300
Tyr Leu Val Ser Ser His Asn Thr Tyr Leu Leu Glu Asp Gln Leu
305                 310                 315                 320
Thr Gly Pro Ser Ser Thr Glu Ala Tyr Ile Arg Ala Leu Cys Lys Gly
                325                 330                 335
Cys Arg Cys Leu Glu Leu Asp Cys Trp Asp Gly Pro Asn Gln Glu Pro
        340                 345                 350
Ile Ile Tyr His Gly Tyr Thr Phe Thr Ser Lys Ile Leu Phe Cys Asp
        355                 360                 365
Val Leu Arg Ala Ile Arg Asp Tyr Ala Phe Lys Ala Ser Pro Tyr Pro
        370                 375                 380
Val Ile Leu Ser Leu Glu Asn His Cys Ser Leu Glu Gln Gln Arg Val
385                 390                 395                 400
Met Ala Arg His Leu Arg Ala Ile Leu Gly Pro Ile Leu Leu Asp Gln
                405                 410                 415
Pro Leu Asp Gly Val Thr Thr Ser Leu Pro Ser Pro Glu Gln Leu Lys
        420                 425                 430
Gly Lys Ile Leu Leu Lys Gly Lys Lys Leu Gly Gly Leu Leu Pro Ala
        435                 440                 445
Gly Gly Glu Asn Gly Ser Glu Ala Thr Asp Val Ser Asp Glu Val Glu
450                 455                 460
Ala Ala Glu Met Glu Asp Glu Ala Val Arg Ser Gln Val Gln His Lys
465                 470                 475                 480
Pro Lys Glu Asp Lys Leu Lys Leu Val Pro Glu Leu Ser Asp Met Ile
                485                 490                 495
Ile Tyr Cys Lys Ser Val His Phe Gly Gly Phe Ser Ser Pro Gly Thr
        500                 505                 510
Ser Gly Gln Ala Phe Tyr Glu Met Ala Ser Phe Ser Glu Ser Arg Ala
        515                 520                 525
Leu Arg Leu Leu Gln Glu Ser Gly Asn Gly Phe Val Arg His Asn Val
        530                 535                 540
Ser Cys Leu Ser Arg Ile Tyr Pro Ala Gly Trp Arg Thr Asp Ser Ser
545                 550                 555                 560
Asn Tyr Ser Pro Val Glu Met Trp Asn Gly Gly Cys Gln Ile Val Ala
                565                 570                 575
Leu Asn Phe Gln Thr Pro Gly Pro Glu Met Asp Val Tyr Leu Gly Cys
        580                 585                 590
Phe Gln Asp Asn Gly Gly Cys Gly Tyr Val Leu Lys Pro Ala Phe Leu
        595                 600                 605
Arg Asp Pro Asn Thr Thr Phe Asn Ser Arg Ala Leu Thr Gln Gly Pro
610                 615                 620
Trp Trp Arg Pro Glu Arg Leu Arg Val Arg Ile Ile Ser Gly Gln Gln
625                 630                 635                 640
Leu Pro Lys Val Asn Lys Asn Lys Asn Ser Ile Val Asp Pro Lys Val
                645                 650                 655
Ile Val Glu Ile His Gly Val Gly Arg Asp Thr Gly Ser Arg Gln Thr
        660                 665                 670
Ala Val Ile Thr Asn Asn Gly Phe Asn Pro Arg Trp Asp Met Glu Phe
        675                 680                 685
Glu Phe Glu Val Thr Val Pro Asp Leu Ala Leu Val Arg Phe Met Val
        690                 695                 700
Glu Asp Tyr Asp Ser Ser Ser Lys Asn Asp Phe Ile Gly Gln Ser Thr
705                 710                 715                 720
Ile Pro Trp Asn Ser Leu Lys Gln Gly Tyr Arg His Val His Leu Leu
                725                 730                 735
Ser Lys Asn Gly Asp Gln His Pro Ser Ala Thr Leu Phe Val Lys Ile
        740                 745                 750
Ser Ile Gln Asp
        755
```

<210> SEQ ID NO 12
<211> LENGTH: 83
<212> TYPE: PRT
<213> ORGANISM: Homo sapiens -continued

```
<400> SEQUENCE: 12

Val Ile Lys Glu Gly Trp Leu Leu Lys Lys Ser Lys Ser Trp Lys Lys
       1               5                  10                  15
      Arg Tyr Phe Val Leu Phe Asn Asn Val Leu Leu Tyr Tyr Lys Asp Ser
                      20                  25                  30
      Lys Lys Pro Lys Gly Ser Ile Pro Leu Ser Gly Cys Gln Val Glu
                  35                  40                  45
      Lys Pro Asp Lys Asn Cys Phe Glu Ile Arg Thr Asp Arg Thr Leu Leu
              50                  55                  60
      Leu Gln Ala Glu Ser Glu Glu Arg Lys Glu Trp Val Lys Ala Ile
       65                  70                  75                  80
      Gln Ser Ala

<210> SEQ ID NO 13
<211> LENGTH: 745
<212> TYPE: PRT
<213> ORGANISM: Homo sapiens

<400> SEQUENCE: 13

Met Gly Leu Thr Glu Asp Glu Asp Val Arg Ala Met Leu Arg Gly Ser
       1               5                  10                  15
      Arg Leu Arg Lys Ile Arg Ser Arg Thr Trp His Lys Glu Arg Leu Tyr
                      20                  25                  30
      Arg Leu Gln Glu Asp Gly Leu Ser Val Trp Phe Gln Arg Arg Ile Pro
                  35                  40                  45
      Arg Ala Pro Ser Gln His Ile Phe Phe Val Gln His Ile Glu Ala Val
              50                  55                  60
      Arg Glu Gly His Gln Ser Glu Gly Leu Arg Arg Phe Gly Gly Ala Phe
       65                  70                  75                  80
      Ala Pro Ala Arg Cys Leu Thr Ile Ala Phe Lys Gly Arg Arg Lys Asn
                      85                  90                  95
      Leu Asp Leu Ala Ala Pro Thr Ala Glu Glu Ala Gln Arg Trp Val Arg
                  100                 105                 110
      Gly Gly Gly Asp Leu Pro Ala Ser Tyr Leu Arg Ala Gly Gly Ser Leu
                  115                 120                 125
      Ala Cys Cys Cys Tyr Phe Leu Ser Thr His Thr Trp Ile His Ser Tyr
              130                 135                 140
      Leu His Arg Ala Asp Ser Asn Gln Asp Ser Lys Met Ser Phe Lys Glu
      145                 150                 155                 160
      Ile Lys Ser Leu Leu Arg Met Val Asn Val Asp Met Asn Asp Met Tyr
                      165                 170                 175
      Ala Tyr Leu Leu Phe Lys Glu Cys Asp His Ser Asn Asn Asp Arg Leu
                  180                 185                 190
      Glu Gly Ala Glu Ile Glu Glu Phe Leu Arg Arg Leu Leu Lys Arg Pro
                  195                 200                 205
      Glu Leu Glu Glu Ile Phe His Gln Tyr Ser Gly Glu Asp Arg Val Leu
              210                 215                 220
      Ser Ala Pro Glu Leu Leu Glu Phe Leu Glu Asp Gln Gly Glu Glu Gly
      225                 230                 235                 240
      Ala Thr Leu Ala Arg Ala Gln Gln Leu Ile Gln Thr Tyr Glu Leu Asn
                      245                 250                 255
      Glu Thr Ala Lys Gln His Glu Leu Met Thr Leu Asp Gly Phe Met Met
                  260                 265                 270
      Tyr Leu Leu Ser Pro Glu Gly Ala Ala Leu Asp Asn Thr His Thr Cys
                  275                 280                 285
      Val Phe Gln Asp Met Asn Gln Pro Leu Ala His Tyr Phe Ile Ser Ser
              290                 295                 300
      Ser His Asn Thr Tyr Leu Thr Asp Ser Gln Ile Gly Gly Pro Ser Ser
      305                 310                 315                 320
      Thr Glu Ala Tyr Val Arg Ala Phe Ala Gln Gly Cys Arg Cys Val Glu
                      325                 330                 335
      Leu Asp Cys Trp Glu Gly Pro Gly Gly Glu Pro Val Ile Tyr His Gly
                  340                 345                 350
      His Thr Leu Thr Ser Lys Ile Leu Phe Arg Asp Val Val Gln Ala Val
                  355                 360                 365
      Arg Asp His Ala Phe Thr Leu Ser Pro Tyr Pro Val Ile Leu Ser Leu
              370                 375                 380
      Glu Asn His Cys Gly Leu Glu Gln Ala Ala Met Ala Arg His Leu
      385                 390                 395                 400
      Cys Thr Ile Leu Gly Asp Met Leu Val Thr Gln Ala Leu Asp Ser Pro
                      405                 410                 415
      Asn Pro Glu Glu Leu Pro Ser Pro Glu Gln Leu Lys Gly Lys Val Leu
                  420                 425                 430
      Val Lys Gly Lys Lys Leu Pro Ala Ala Arg Ser Glu Asp Gly Arg Ala
                  435                 440                 445
      Leu Ser Asp Arg Glu Glu Glu Glu Asp Asp Glu Glu Glu Glu
```

-continued

```
        450                 455                 460
    Glu Val Glu Ala Ala Ala Gln Arg Arg Leu Val Arg Ala Gly Met Asp
    465                 470                 475                 480
    Leu Pro Gly Ala Val Gly Pro Gly Cys Val Leu Pro Arg His Pro Pro
                        485                 490                 495
    Ala Thr Leu His Pro Ala Pro Asn Ala Pro Gln Pro Cys Gln Val Ser
                    500                 505                 510
    Ser Leu Ser Glu Arg Lys Ala Lys Lys Leu Ile Arg Glu Ala Gly Asn
                515                 520                 525
    Ser Phe Val Arg His Asn Ala Arg Gln Leu Thr Arg Val Tyr Pro Leu
                530                 535                 540
    Gly Leu Arg Met Asn Ser Ala Asn Tyr Ser Pro Gln Glu Met Trp Asn
    545                 550                 555                 560
    Ser Gly Cys Gln Leu Val Ala Leu Asn Phe Gln Thr Pro Gly Tyr Glu
                        565                 570                 575
    Met Asp Leu Asn Ala Gly Arg Phe Leu Val Asn Gly Gln Cys Gly Tyr
                    580                 585                 590
    Val Leu Lys Pro Ala Cys Leu Arg Gln Pro Asp Ser Thr Phe Asp Pro
                595                 600                 605
    Glu Tyr Pro Gly Pro Pro Arg Thr Thr Leu Ser Ile Gln Val Leu Thr
            610                 615                 620
    Ala Gln Gln Leu Pro Lys Leu Asn Ala Glu Lys Pro His Ser Ile Val
    625                 630                 635                 640
    Asp Pro Leu Val Arg Ile Glu Ile His Gly Val Pro Ala Asp Cys Ala
                        645                 650                 655
    Arg Gln Glu Thr Asp Tyr Val Leu Asn Asn Gly Phe Asn Pro Arg Trp
                    660                 665                 670
    Gly Gln Thr Leu Gln Phe Gln Leu Arg Ala Pro Glu Leu Ala Leu Val
                675                 680                 685
    Arg Phe Val Val Glu Asp Tyr Asp Ala Thr Ser Pro Asn Asp Phe Val
            690                 695                 700
    Gly Gln Phe Thr Leu Pro Leu Ser Ser Leu Lys Gln Gly Tyr Arg His
    705                 710                 715                 720
    Ile His Leu Leu Ser Lys Asp Gly Ala Ser Leu Ser Pro Ala Thr Leu
                        725                 730                 735
    Phe Ile Gln Ile Arg Ile Gln Arg Ser
                    740                 745
```